(12) United States Patent
Hickey

(10) Patent No.: US 11,628,268 B1
(45) Date of Patent: Apr. 18, 2023

(54) DEVICE FOR OPERATIVELY COUPLING TO A STRUCTURE AND DIRECTING GAS FLOW AND A METHOD OF USE THEREOF

(71) Applicant: Sergio Hickey, Pittsburgh, PA (US)

(72) Inventor: Sergio Hickey, Pittsburgh, PA (US)

(73) Assignee: Sergio Hickey, Pittsburgh, PA (US)

( * ) Notice: Subject to any disclaimer, the term of this patent is extended or adjusted under 35 U.S.C. 154(b) by 0 days.

(21) Appl. No.: 17/996,135

(22) PCT Filed: Mar. 29, 2022

(86) PCT No.: PCT/US2022/022356
§ 371 (c)(1),
(2) Date: Oct. 13, 2022

(87) PCT Pub. No.: WO2022/212382
PCT Pub. Date: Oct. 6, 2022

Related U.S. Application Data

(60) Provisional application No. 63/168,036, filed on Mar. 30, 2021.

(51) Int. Cl.
| | | |
|---|---|---|
| A61M 16/08 | (2006.01) | |
| A61B 1/015 | (2006.01) | |
| A61B 1/00 | (2006.01) | |
| A61B 1/267 | (2006.01) | |

(52) U.S. Cl.
CPC ..... *A61M 16/0816* (2013.01); *A61B 1/00128* (2013.01); *A61B 1/015* (2013.01); *A61B 1/267* (2013.01); *A61M 16/0875* (2013.01); *A61M 2202/0208* (2013.01)

(58) Field of Classification Search
CPC .......... A61B 1/267; A61B 1/00; A61B 1/015; A61B 1/12; A61B 1/012; A61B 1/00066; A61B 1/00091; A61B 1/00105; A61B 1/127; A61M 16/08
See application file for complete search history.

(56) References Cited

U.S. PATENT DOCUMENTS

| | | |
|---|---|---|
| 3,815,606 A | 6/1974 | Mazal |
| 4,949,716 A | 8/1990 | Chenoweth |
| 10,004,384 B2 | 6/2018 | Oginski et al. |
| 10,849,488 B2 | 12/2020 | Pecherer |

FOREIGN PATENT DOCUMENTS

KR     10-1245435 B1     3/2013

OTHER PUBLICATIONS

International Search Report and Written Opinion of the International Searching Authority for International Application No. PCT/US2022/022356 dated Jul. 14, 2022.

*Primary Examiner* — Christopher J Beccia
(74) *Attorney, Agent, or Firm* — K&L Gates LLP

(57) ABSTRACT

A device for operatively coupling to a structure and directing gas flow and a method of use thereof are provided. The device comprises an attachment apparatus, a gas outlet nozzle, and a. housing. The attachment apparatus is configured to operatively couple to the structure. The gas outlet nozzle is configured to direct a flow of gas to a desired location. The housing is operatively coupled to the attachment apparatus and the gas flow nozzle.

19 Claims, 19 Drawing Sheets

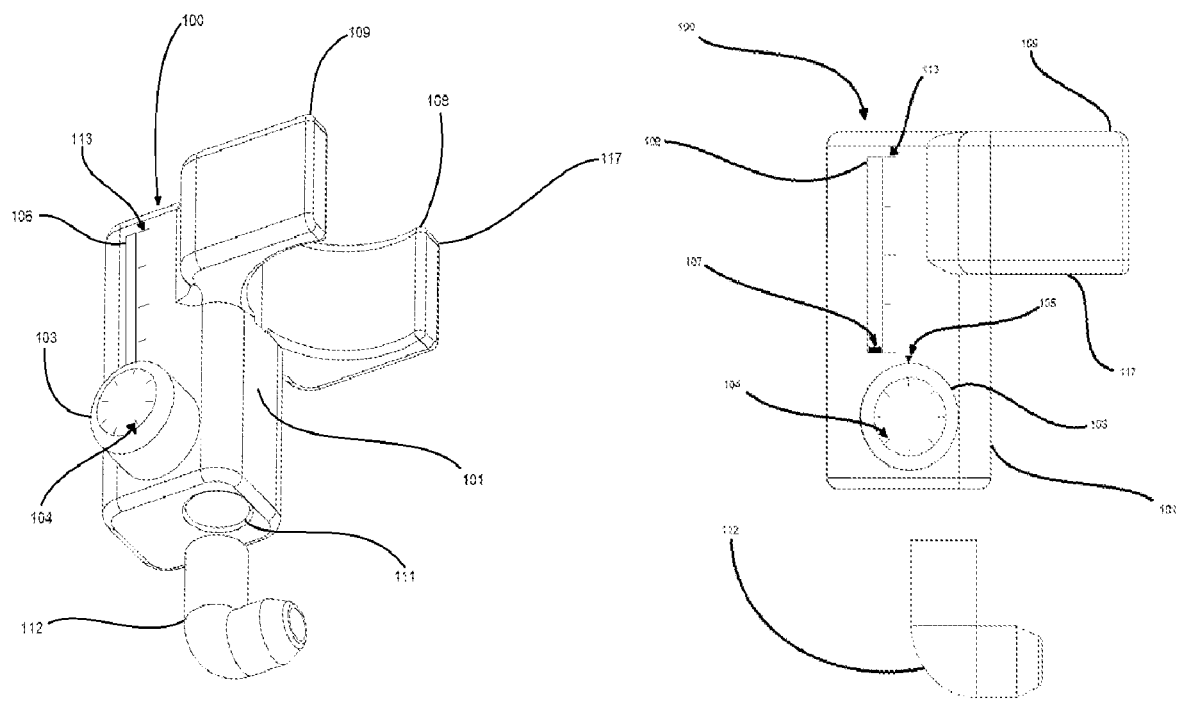
Figure 1
Figure 2
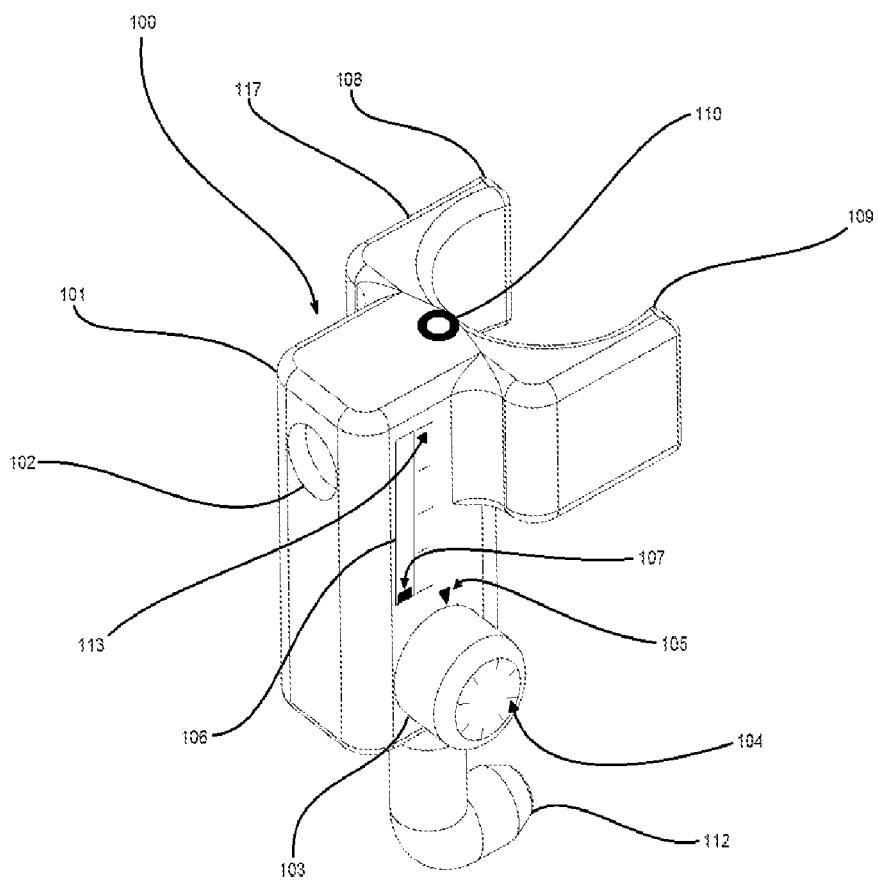
Figure 3

US 11,628,268 B1

DEVICE FOR OPERATIVELY COUPLING TO A STRUCTURE AND DIRECTING GAS FLOW AND A METHOD OF USE THEREOF

CROSS-REFERENCE TO RELATED APPLICATIONS

This application is a nationalization application of international Patent Application No. PCT/US2022/022356, filed Mar. 29, 2022, which claims priority to U.S. Provisional Patent Application No. 63/168,036, which was filed on Mar. 30, 2021. The contents of each of which air hereby incorporated by reference into this specification.

FIELD

The present application discloses a device for operatively coupling to a structure and directing gas flow and a method of use thereof.

BACKGROUND

Typically, when general anesthesia is induced by anesthesiologists, intensivists, emergency physicians, or paramedics for the purpose of inserting a breathing tube prior to surgery, or for lifesaving purposes, patients enter a critical period during which they stop breathing—known as apnea. This can be a beneficial step in facilitating the placement of a breathing tube, also known as endotracheal intubation. During this period of apnea prior to endotracheal intubation, blood oxygen levels may rapidly decline to dangerous levels. As such, the airway manager should secure the airway as quickly as possible, usually through the insertion of a laryngoscope that allows for the visualization of the glottis and larynx, through which an endotracheal tube will be passed and inserted into the trachea. Apneic oxygenation is a method by which oxygen levels can be maintained by administering flows of oxygen and positive pressure to the airway during endotracheal intubation. Through apneic oxygenation, patients may remain oxygenated significantly longer, giving airway managers the time needed to secure the airway after the induction of anesthesia without oxygen levels dropping to dangerously low levels. Current methods for apneic oxygenation while securing an airway or inducing anesthesia can be ineffective, costly, physically cumbersome, and thus either largely inaccessible or undesirable for most airway managers.

SUMMARY

In one aspect, a device for operatively coupling to a structure and directing gas flow is provided. The device comprises an attachment apparatus, a gas outlet nozzle, and a housing. The attachment apparatus is configured to operatively couple to the structure. The gas outlet nozzle is configured to direct a flow of gas to a desired location. The housing is operatively coupled to the attachment apparatus and the gas flow nozzle.

In another aspect, a device for operatively coupling to a laryngoscope for administration of a positive pressure to the airway of a mammal is provided. The device comprises a housing, an attachment apparatus, and a gas glow nozzle. The gas flow inlet port is configured to receive a tube. The attachment apparatus is operatively coupled to the housing and configured to operatively couple to the laryngoscope. The attachment apparatus comprises a first clamp arm and a second clamp arm. The gas flow nozzle is operatively coupled to the housing and configured to direct a flow of gas down a longitudinal axis of a buccal aspect of a blade of laryngoscope. The gas flow nozzle comprises a gas flow outlet port. A gas flow conduit is defined in the housing and the gas flow nozzle to form fluid communication between the gas flow inlet port and the gas flow outlet port.

In yet another aspect, a device for operatively coupling to a laryngoscope for administration of a positive pressure to the airway of a mammal is provided. The device comprises a housing, an attachment apparatus, and a gas flow nozzle. The housing comprises a gas flow inlet port configured to receive a tube. The attachment apparatus is operatively coupled to the housing and configured to operatively couple to the laryngoscope. The attachment apparatus comprises a first clamp arm and a second clamp arm that are configured to friction fit to the laryngoscope. The gas flow nozzle is operatively coupled to the housing and configured to direct a flow of gas down a longitudinal axis of a buccal aspect of a blade of laryngoscope. The gas flow nozzle comprising a gas flow outlet port. A gas flow conduit (e.g., a channel) is defined in the housing and the gas flow nozzle to form fluid communication between the gas flow inlet port and the gas flow outlet port. The gas flow inlet port, gas flow outlet port, and gas flow conduit are sized and configured to enable a gas flow in a range of greater than 0 liters per minute to 250 liters per minute as measured with a 54 pounds per square inch gauge pressure feed at the gas flow inlet port and the gas flow outlet port open to atmospheric pressure. The housing, the attachment apparatus, and the gas flow nozzle are integral.

In yet a further aspect, a method of laryngoscopy is provided. The method comprises operatively coupling a gas source to a simple laryngoscope or video laryngoscope for administration of a positive pressure to the airway of a mammal utilizing a device according to the present disclosure. The method further comprises insufflating the airway of the mammal with the device.

It will be understood that the inventions disclosed and described in this specification are not limited to the aspects summarized in this Summary. The reader will appreciate the foregoing details, as well as others, upon considering the following detailed description of various non-limiting and non-exhaustive aspects according to this specification.

BRIEF DESCRIPTION OF THE DRAWINGS

The features and advantages of the examples presented herein, and the manner of attaining them, will become more apparent, and the examples will be better understood, by reference to the following description taken in conjunction with the accompanying drawings, wherein:

FIG. 1 is a right inferior isometric view of an example of a device according to the present disclosure;

FIG. 2 is a right side orthographic view of the device of FIG. 1;

FIG. 3 is a right superior isometric view of the device of FIG. 1;

Corresponding reference characters indicate corresponding parts throughout the several views. The exemplifications set out herein illustrate certain embodiments, in one form, and such exemplifications are not to be construed as limiting the scope of the appended claims in any manner.

DETAILED DESCRIPTION

Figure 4:
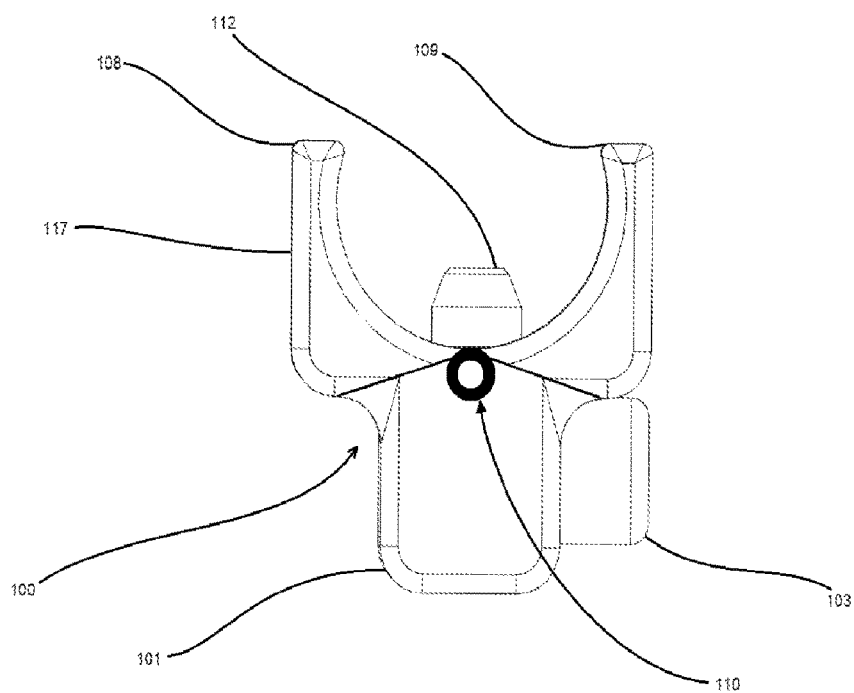
FIG. 4 is a top orthographic view of the device of FIG. 1.
Figure 5:
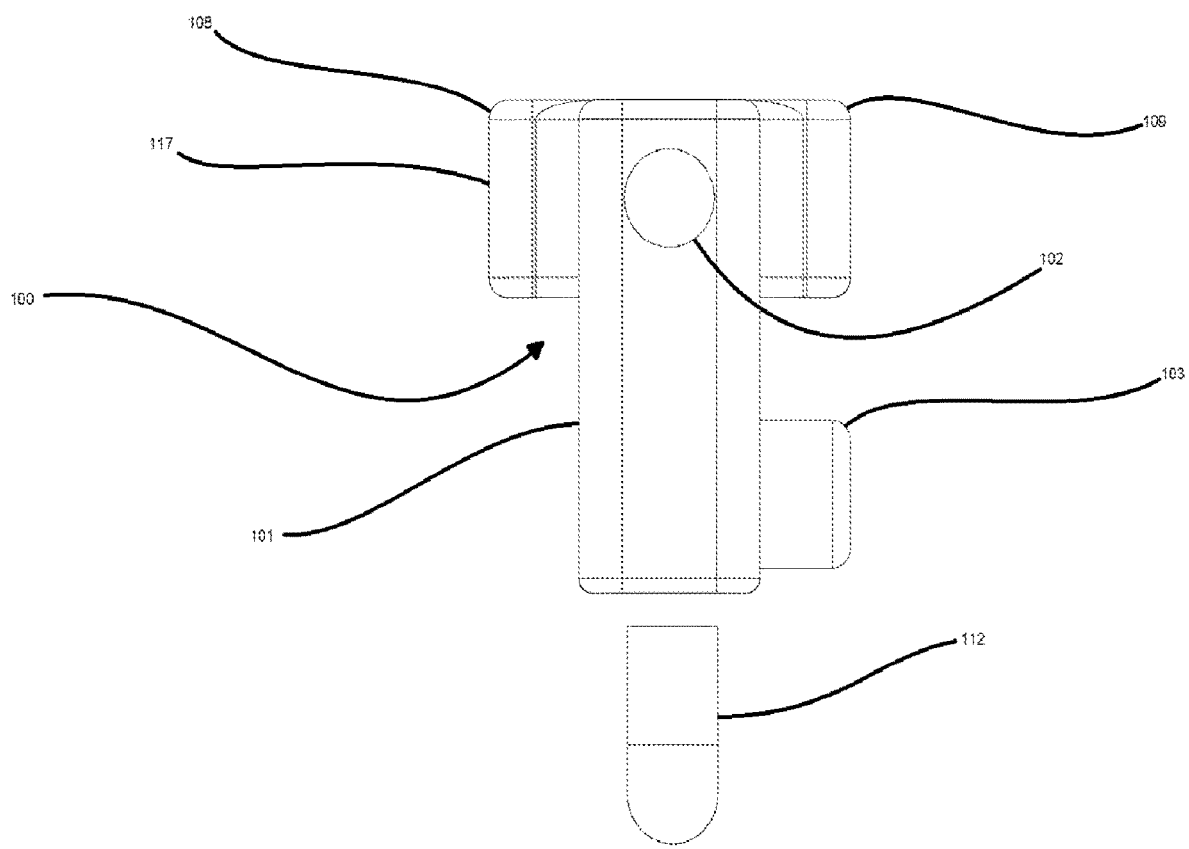
FIG. 5 is a rear orthographic view of the device of FIG. 1.

Various examples are described and illustrated herein to provide an overall understanding of the present invention. The various examples described and illustrated herein are non-limiting and non-exhaustive. Thus, the invention is not limited by the description of the various non-limiting and non-exhaustive examples disclosed herein. Rather, the invention is defined solely by the claims. The features and characteristics illustrated and/or described in connection with various examples may be combined with the features and characteristics of other examples. Such modifications and variations are intended to be included within the scope of this specification. As such, the claims may be amended to recite any features or characteristics expressly or inherently described in, or otherwise expressly or inherently supported by, this specification. Further, Applicant reserves the right to amend the claims to affirmatively disclaim features or characteristics that may be present in the prior art. The various examples disclosed and described in this specification can comprise, consist of, or consist essentially of the features and characteristics as variously described herein.

The device for coupling to a structure and directing gas flow according to the present disclosure can be well suited for apneic oxygenation while mounted on any laryngoscope or airway device with bespoke or universal clamps that can remove barriers to apneic oxygenation during endotracheal intubation or direct or indirect laryngoscopy for other treatments or examinations. The more accessible and effective apneic oxygenation produced by the device for coupling to a structure and directing gas flow according to the present disclosure can improve the safety profile of potentially any airway manipulation, including but not limited to laryngoscopy, endotracheal intubation, bronchoscopy, cricothyrotomy, tracheostomy, jet ventilation, and airway examination.

In various examples, the present disclosure provides a device with an integrated gas flow regulator that can be secured to any laryngoscope or other airway devices through a bespoke or universal clamping apparatus. The gas flow regulator can accept oxygen from hospital central oxygen supplies, or small portable supply units.

In the following detailed description, the device according to the present disclosure can be a universally mountable laryngoscope gas flow regulator. It should be noted that while the airway device will commonly find use in laryngoscopy during the induction of anesthesia and endotracheal intubation, it can be a useful device for apneic oxygenation—and thus improving patient safety—during an episode of laryngoscopy or airway manipulation by any practitioner for any treatment or examination.

The device according to the present disclosure can comprise a gas flow regulator and directable gas flow nozzle that can be mounted onto any laryngoscope or other airway device and direct flows of oxygen or gas into the airways of humans or animals, with flows that can be modulated with a gas flow controller. In other examples, the device may not comprise a gas flow regulator. In various examples, the device may comprise a gas flow nozzle that is fixed relative to the housing.

An example of a device 100 for operatively coupling to a structure and directing gas flow according to the present disclosure is illustrated in FIG. 1, FIG. 2, FIG. 3, FIG. 4, and FIG. 5. The device 100 comprises a housing 101, an attachment apparatus 117 operatively coupled to the housing 101, and a gas flow nozzle 112 operatively coupled to the housing 101. The attachment apparatus 117 can be integral with the housing 101 or the attachment apparatus 117 can be attached to the housing 101 by various means, such as, for example, a fastener, an adhesive, a friction fit, or the like. The gas flow nozzle 112 can be integral with the housing 101 or the gas flow nozzle can be attached to the housing 101 by various means, such as, for example, a fastener, an adhesive, a friction fit, or the like. In various examples, the device 100 can comprise a gas flow regulator 103, and a gas flow rate indicator 106. The device 100 can be infant sized, child sized, and adult sized based on the desired application.

The gas flow nozzle 112 can be a directable gas flow nozzle that can be mounted onto specific laryngoscopes and direct flows of oxygen or gas into the airways of humans or animals, with flows that can be modulated with a gas flow controller that is separate from the device 100.

An example of a device 100a for operatively coupling to a structure and directing gas flow according to the present disclosure is illustrated in FIG. 15, FIG. 16, FIG. 17, FIG. 18, FIG. 19, FIG. 20, FIG. 21, FIG. 22, and FIG. 23. The device 100 can administer a positive pressure (i.e., a gas pressure greater than ambient pressure (>0 PSIG)) to the airway (e.g., upper airway, lower airway, a combination thereof) of a mammal (e.g., a human). For example, the device 100 can administer a gas comprising oxygen (e.g., pure oxygen, an air blend (21 mol % oxygen)) to the airway of a mammal. The device 100a comprises a housing 101a, an attachment apparatus 117a operatively coupled to the housing 101a, and a gas flow nozzle 112a. The attachment apparatus 117a can be integral with the housing 101a or the attachment apparatus 117a can be attached to the housing 101a by various means, such as, for example, a fastener, an adhesive, a friction fit, or the like. The gas flow nozzle 112a can be integral with the housing 101a or the gas flow nozzle can be attached to the housing 101a by various means, such as, for example, a fastener, an adhesive, a friction fit, or the like. The housing can comprise a gas flow inlet port 102a that can be configured to receive a tube. For example, the gas flow inlet port 102a can be substantially round and suitable to accept a flexible polymeric tube having an internal diameter in a range of of ⅛" to ½" (e.g., 3/16"). The gas flow nozzle can comprise a gas flow outlet port 111a. The gas flow outlet port 111a can comprise an internal diameter in a range of ⅛" to 1". The housing 101a, the attachment apparatus 117a, and the gas flow nozzle 112a can be integral (e.g., formed from a single piece) or they can be separately formed.

The device 100 and/or 100a can be coupled with an aiming tool (e.g., laser pointer, or reticle or crosshairs applied to the video feed of a video laryngoscope, etc) to indicate the directionality of the flow of gas leaving the device 100 and/or 100a.

The device 100a can be infant sized, child sized, and adult sized based on the desired application. All following descriptions contained herein of use and function for device 100, and its components 101, 102, 111, and 117 may also necessarily serve as descriptions for use and function of device 100a, and its components 101a, 102a, 111a, and 117a.

A gas flow conduit can be defined in the housing 101 and the gas flow nozzle 112 to form fluid communication between the gas flow inlet port 102 to the gas flow outlet port 111. For example, the gas flow conduit can be a channel within the housing 101 and the gas nozzle 112 which can be tubular and optionally round, square, or other shape in a cross-sectional view.

The gas flow regulator 103 can be integral with the housing 101 or separate from the housing 101. In various examples where the gas flow regulator 103 is integral with the housing 101, the gas flow regulator 103 can control the rate of gas from the gas flow inlet port 102 to the gas flow outlet port 111 through the gas flow conduit. In various examples where the gas flow regulator 103 is separate from the housing 101, the gas flow regulator 103 can control the gas flow being introduced to gas flow inlet port 102 from the gas source 115, and/or gas flow that is directly being introduced to the gas flow nozzle 112. The gas flow nozzle 112 creates flows of gas that move along the length of the laryngoscope blade, or other airway device.

The gas flow nozzle 112 of device 100 can be made longer as shown by nozzle 112a of device 100a and can conform to the length of the blade 120 of a laryngoscope 119 and does not necessarily require a separate gas flow nozzle. The gas flow outlet 111a can create a flow of gas that moves along the a longitudinal axis of the blade 120 of the larygscope 119, or other airway device. The extended length of the gas flow nozzle 112 can allow for gas flows to exit the device 100a more closely to the desired anatomic gas entry point, such as a glottic opening, than thus convey gas more effectively.

The gas flow inlet port 102 can receive gas from a portable or permanent oxygen sources of varying pressurization. Gas tubing may be connected to the gas flow inlet port through wedging, locking, rotation over threading, or the like.

The gas flow outlet port 111 may be secured to the gas flow nozzle 112 and/or any gas outlet tract through wedging, locking, rotation over threading or the like.

The attachment apparatus 117 is configured to operatively couple to a structure such as, for example, an airway management device such as, for example, a laryngoscope, video laryngoscope, bronchoscope, endotracheal tube, or other airway management or examination apparatus. The attachment apparatus 117 can comprise a left clamp arm 108, a right clamp arm 109, and optionally a clamp hinge 110. For example, the attachment apparatus 117 can be operatively coupled to a handle of the laryngoscope or other structure on the laryngoscope by pivoting the left clamp arm 108 and the right clamp arm 109 about the clamp hinge 110 to accept the handle or other structure and then pivoting the left clamp arm 108 and the right clamp arm 109 to exert a clamping force on the handle or other structure. This is demonstrated in FIG. 1, FIG. 2, FIG. 3, FIG. 4, and FIG. 5.

Figure 21:
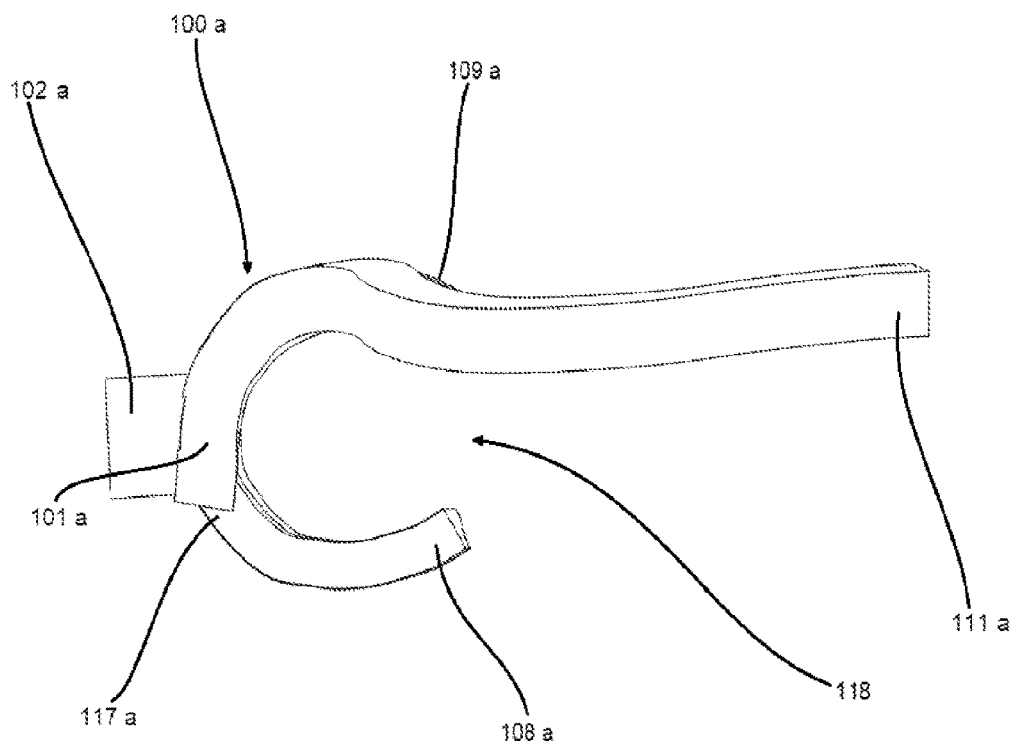
FIG. 21 is a bottom orthographic view of the device of FIG. 15.
Figure 22:
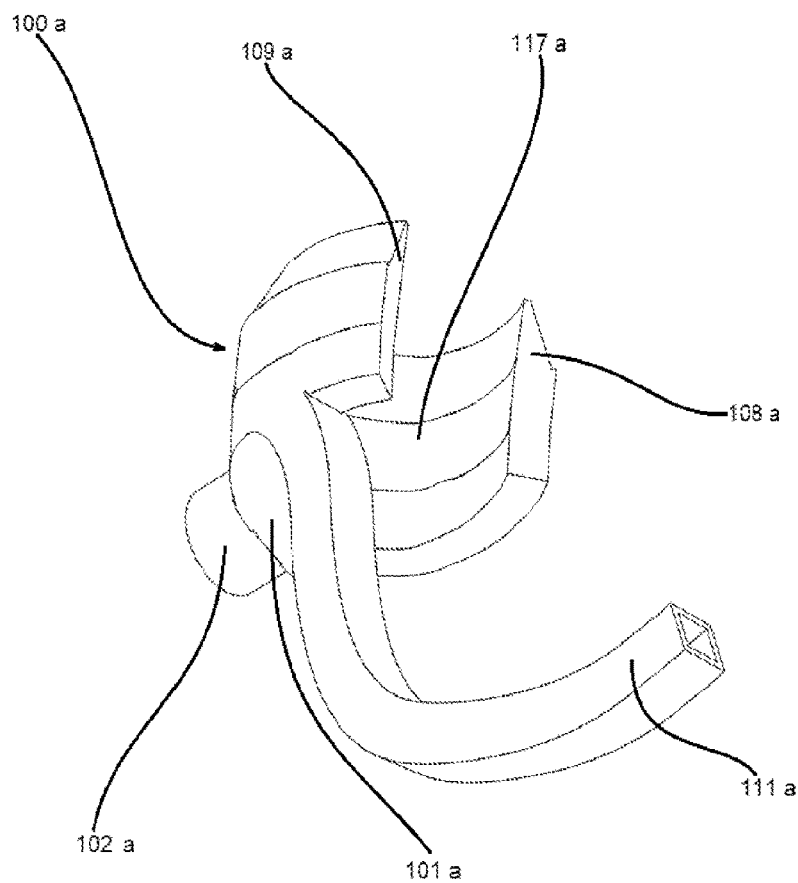
FIG. 22 is a right anteroinferior isometric view of the device of FIG. 15.
Figure 23:
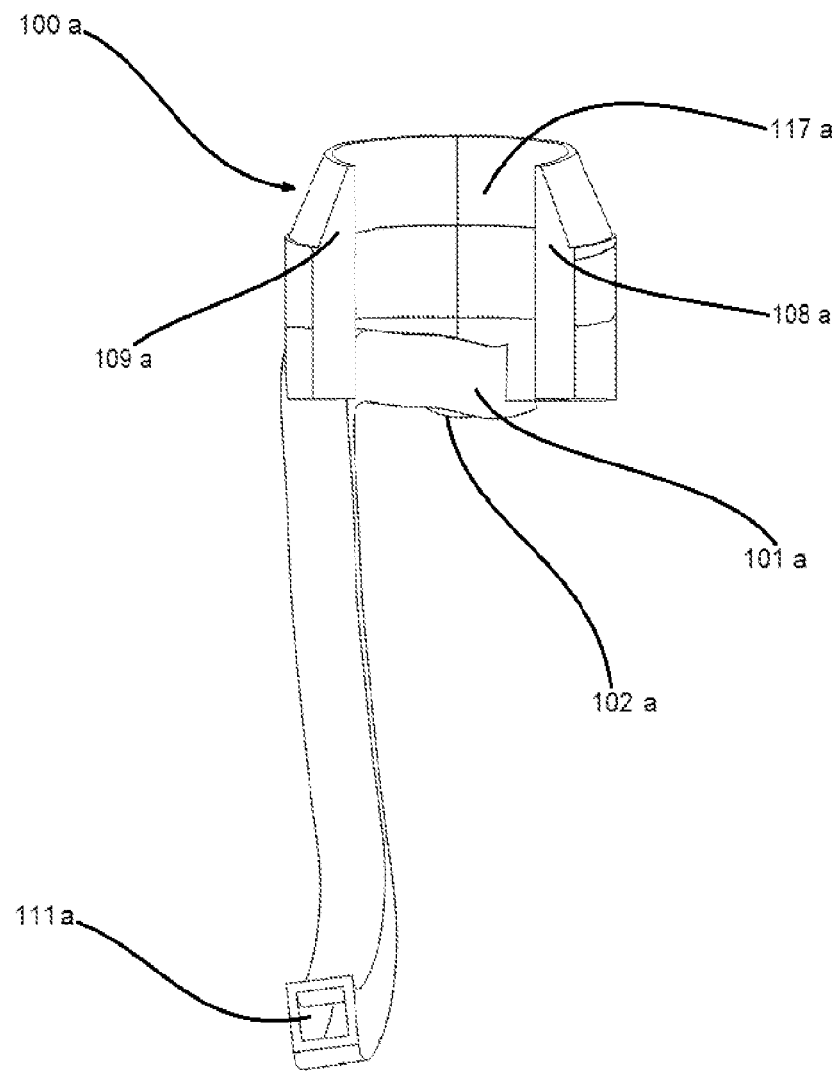
FIG. 23 is a front orthographic view of the device of FIG. 15.
Figure 24:
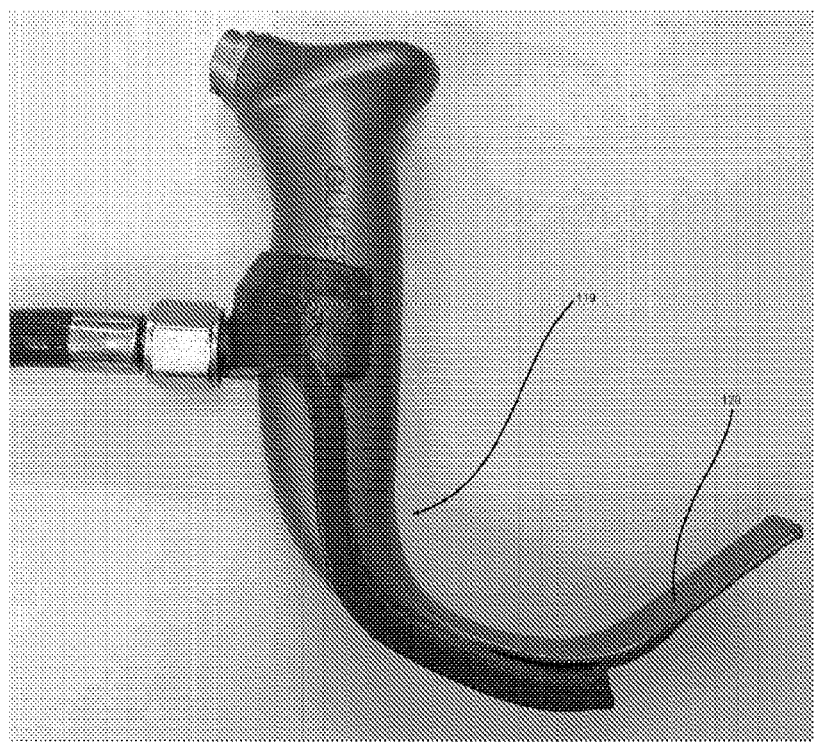
FIG. 24 is a photograph from a right-sided perspective of the device of FIG. 15 operatively secured to a laryngoscope.
Figure 25:
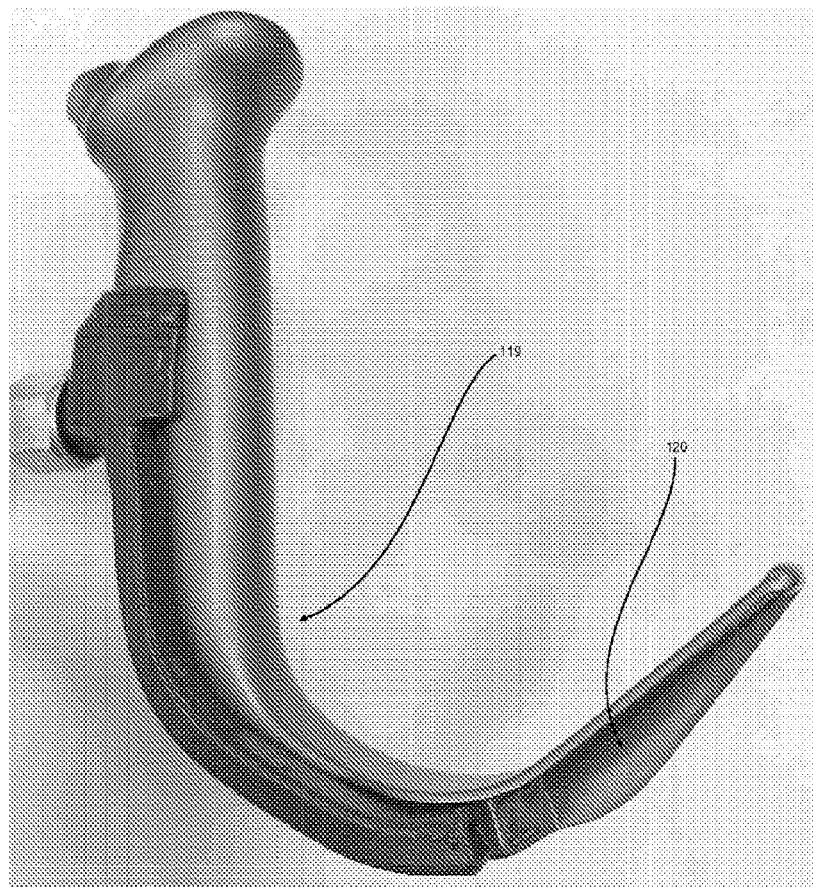
FIG. 25 is a photograph from a front right-sided perspective of the device of FIG. 15 operatively secured to a laryngoscope.
Figure 26:
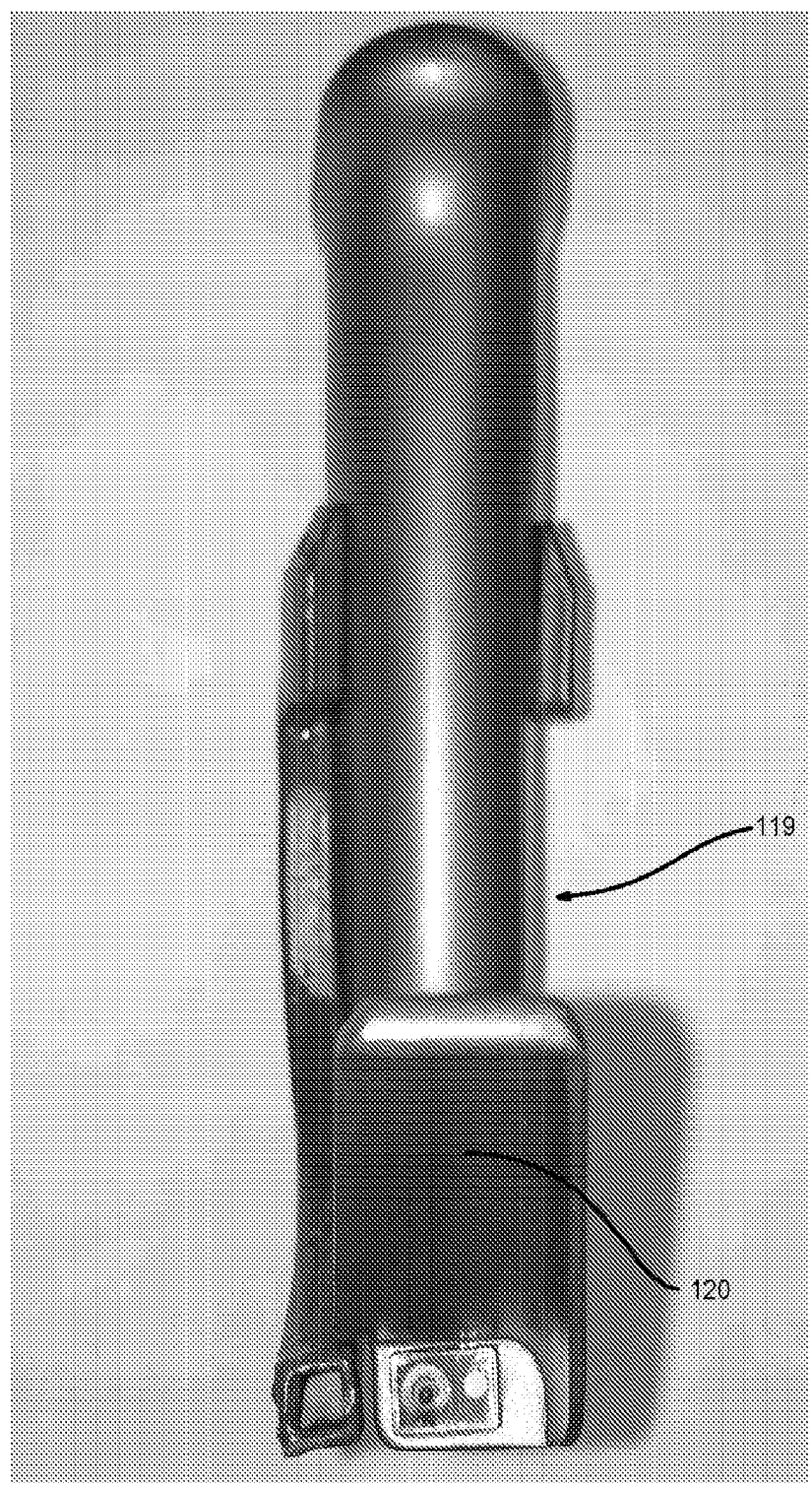
FIG. 26 is a photograph from a frontal perspective of the device of FIG. 15 operatively secured to a laryngoscope.
Figure 27:
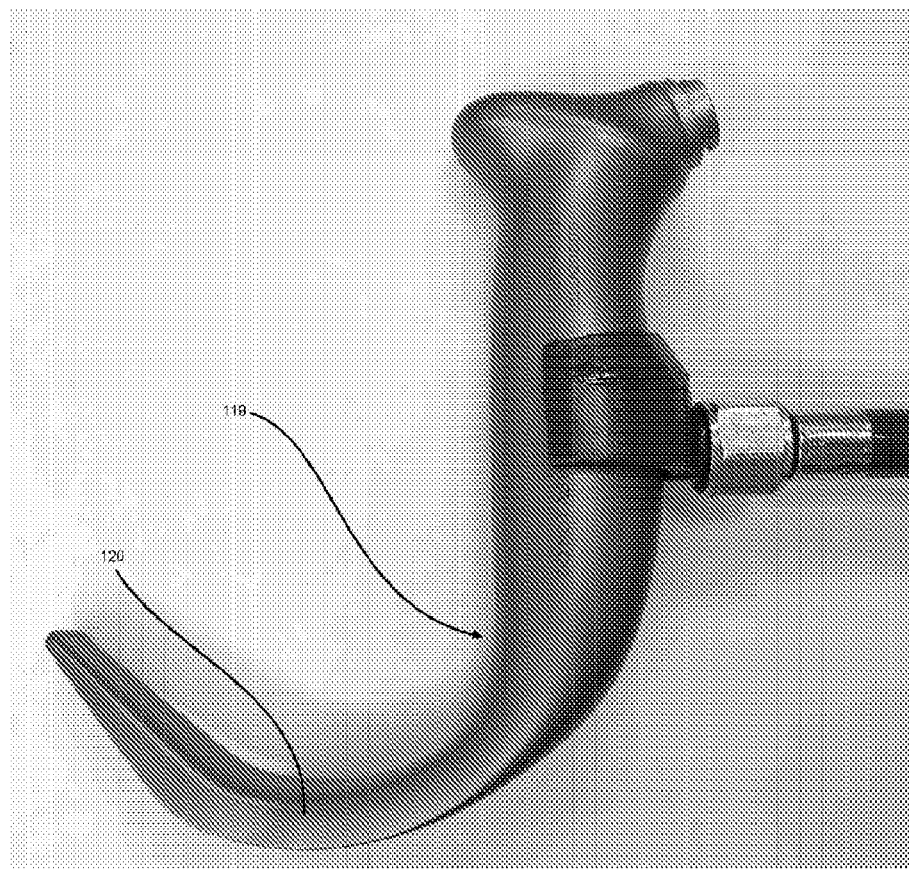
FIG. 27 is a photograph from a left-sided perspective of the device of FIG. 15 operatively secured to a laryngoscope.

The attachment apparatus 117 can be a solid rigid structure that is made with a snap to fit mechanism, as is depicted in FIG. 6, FIG. 7, FIG. 8, and FIG. 9. 117a also demonstrates a snap to fit attachment apparatus, as is depicted in FIG. 15, FIG. 16, FIG. 17, FIG. 18, FIG. 19, FIG. 20, FIG. 21, FIG. 22, FIG. 23, FIG. 24, FIG. 25, FIG. 25, and FIG. 27. As illustrated on device 100a, the left clamp arm 108a and the right clamp arm 109a do not comprise a clamp hinge and are fixed to the housing 101. The left clamp arm 108a and right clamp arm 109a can be configured to friction fit to the laryngoscope 119. In various examples, the left clamp arm 108a and the right clamp arm 109a are each curved inward towards the other, as depicted in FIG. 21. For example, the left clamp arm 108a can be concave relative to the right clamp arm 109a and the right clamp arm 109a can be concave relative to the left clamp arm 108a. The left clamp arm 108a and right clamp arm 109a can be made of a material with enough resiliency to increase an opening 118 between the left clamp arm 108a and the right clamp arm 109a to accept a structure on the laryngoscope and spring back to exert a force on the structure. Further, the attachment apparatus could be operatively coupled to a laryngoscope magnetically. The attachment apparatus 117 may be secured to the laryngoscope handle, laryngoscope handle neck, or to the base of the laryngoscope blade. Thus, the attachment apparatus 117 can be secured to the laryngoscope such that the gas flow nozzle 112 is positioned with respect to the laryngoscope and can direct gas along the blade of the laryngoscope to a desired location. The attachment apparatus 117 may be spring loaded, molded to fit specific airway devices, magnetically mounted, or use any number of other methods or combination of methods.

The gas flow regulator 103 can be configured with regulator flow indicators 104 that can be used to determine the position of the gas flow regulator 103 relative to the indicator 105. Thus, the user can set a desired gas flow by rotating the gas flow regulator 103 until a desired alignment between the controller flow indicators 104 and the indicator 105 is achieved. The gas flow regulator 103 can adjust the gas flow rate through the device 100. In various examples, the gas flow regulator 103 can be adjusted to control the gas flow rate through the gas flow inlet port 102, gas flow outlet port 111, and gas flow conduit. In certain examples, the gas flow inlet port 102, gas flow outlet port 111, and gas flow conduit can be sized and configured to a gas flow rate of greater than 0 liters per minute (LPM), such as, for example, greater than 1 LPM, greater than 2 LPM, greater than 3 LPM, greater than 5 LPM, greater than 10 LPM, greater than 25 LPM, greater than 50 LPM, greater than 75 LPM, or greater than 100 LPM. In certain examples, the gas flow inlet port 102, gas flow outlet port 111, and gas flow conduit can be sized and configured to enable a gas flow rate of no greater than 250 LPM, such as, for example, no greater than 200 LPM, no greater than 150 LPM, no greater than 100 LPM, no greater than 75 LPM, no greater than 50 LPM, no greater than 25 LPM, or no greater than 10 LPM. For example, the gas flow inlet port 102, gas flow outlet port 111, and gas flow conduit can be sized and configured to enable a gas flow rate in a range of greater than 0 LPM to 250 LPM, such as, for example, greater than 0 LPM to 200 LPM, greater than 0 LPM to 200 LPM, greater than 0 LPM to 100 LPM, 1 LPM to 250 LPM, 25 LPM to 250 LPM, 1 LPM to 100 LPM, 10 LPM to 100 LPM, or 25 LPM to 100 LPM. The gas flow rate can be measured with a 54 pounds per square inch gauge pressure feed at the gas flow inlet port 102 and the gas flow nozzle 112 open to atmospheric pressure.

In certain examples, the gas flow inlet port 102, gas flow outlet port 111, and gas flow conduit can be sized and configured to enable a gas flow at a pressure of at least 0 pounds per square inch atmospheric (PSIG), such as, for example, greater than 0 PSIG, at least 1 PSIG, at least 2 PSIG, at least 3 PSIG, at least 5 PSIG, at least 10 PSIG, at least 14.6 PSIG, at least 25 PSIG, at least 50 PSIG, at least 53 PSIG, at least 54 PSIG, at least 55 PSIG, at least 60 PSIG, at least 75 PSIG, at least 100 PSIG, at least 1000 PSIG, or at least 2000 PSIG. In various examples, the gas flow inlet port 102, gas flow outlet port 111, and gas flow conduit can be sized and configured to enable a gas flow at a pressure of no greater than 3000 PSIG, such as, for example, no greater than 2500 PSIG, no greater than 2200 PSIG, no greater than 2000 PSIG, no greater than 1000 PSIG, no greater than 500 PSIG, no greater than 200 PSIG, no greater than 125 PSIG, no greater than 100 PSIG, no greater than 75 PSIG, no greater than 60 PSIG, no greater than 55 PSIG no greater than 54 PSIG, no greater than 53 PSIG, no greater than 50 PSIG, or no greater than 25 PSIG. For example, the gas flow inlet port 102, gas flow outlet port 111, and gas flow conduit can be sized and configured to enable a gas flow at pressure in a range of 0 PSIG to 3000 PSIG, such as, for example, 0 PSIG to 200 PSIG, 1 PSIG to 125 PSIG, 5 PSIG to 100 PSIG, 25 PSIG to 75 PSIG, or 50 PSIG to 60 PSIG.

The gas flow rate indicator 106 can visually indicate the gas flow rate through the housing 101. For example, the gas flow indicator 106 can house a bobbin or float 107 that can move based on the gas flow rate in the gas flow conduit residing in the housing 101. The gas flow rate indicator 106 can be configured with flow rate indictor markers 113 to determine approximate gas flow rates. In various examples, the flow rate indicator markers 113 can be numeric. The position of the bobbin or float 107 relative to the flow rate indicator markers 113 can be used by the operator to determine the gas flow rate within the housing 101 based on the numeric marking. Thus, the output gas flow rate through the gas flow outlet port 111 can be determined based on the bobbin or float 107. In various examples, the device 100 can be manufactured without a gas flow rate indicator 106, bobbin or float 107, and/or flow rate indicator markings 113.

Figure 11:
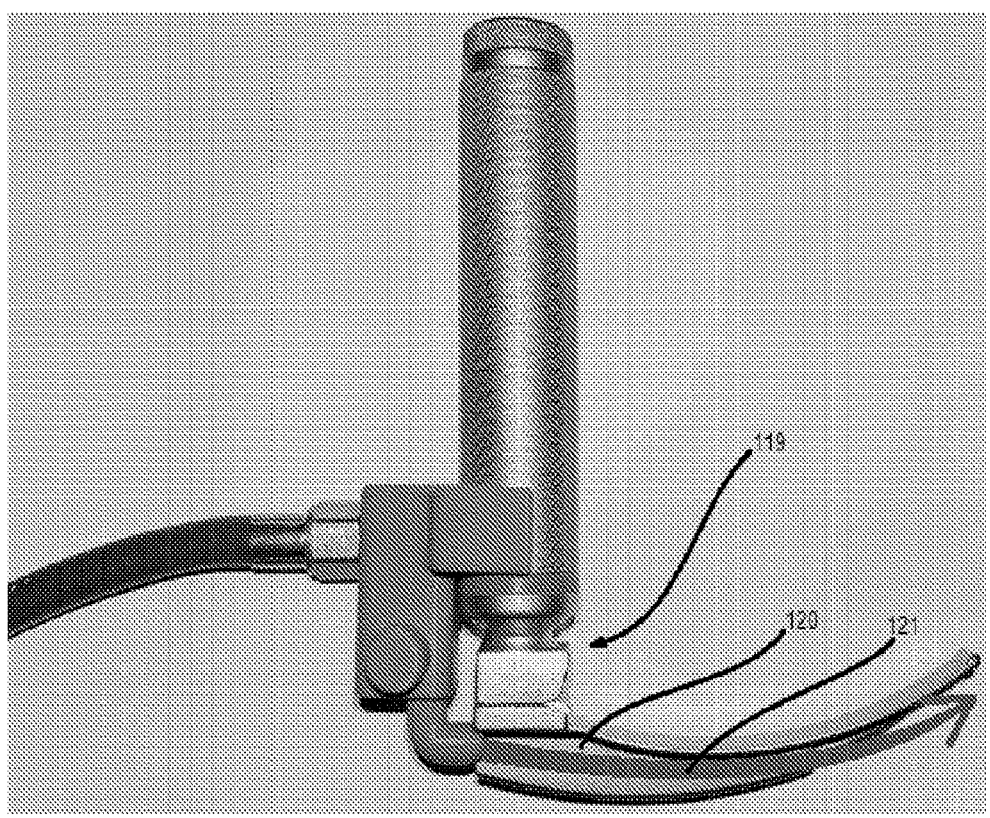
FIG. 11 is a photograph of an example of a device according to the present disclosure operatively coupled to a laryngoscope whilst having gas flow tubing secured to the gas flow inlet port, and while directing gas longitudinally along the buccal aspect of the laryngoscope blade.

The gas flow nozzle 112 may be secured to the housing 101 to direct outgoing gas to a desired location. The gas flow nozzle 112 may be secured to the housing 101 through wedging, locking, rotation over threading, or the like. The gas flow nozzle 112 may be secured to the housing 101 temporarily or permanently, becoming integral with an outlet on the housing 101 through gluing, plastic welding, integral forming, or the like. The gas flow nozzle 112 can be shaped and configured to direct outflowing gas from the gas flow outlet port 111 to a desired location, such as, for example, a region of an airway of a patient. The gas flow nozzle 112 may direct gas flows longitudinally along the inferior aspect 121 of the blade 120 of a laryngoscope 119, as indicated by the arrow in FIG. 11.

Figure 12:
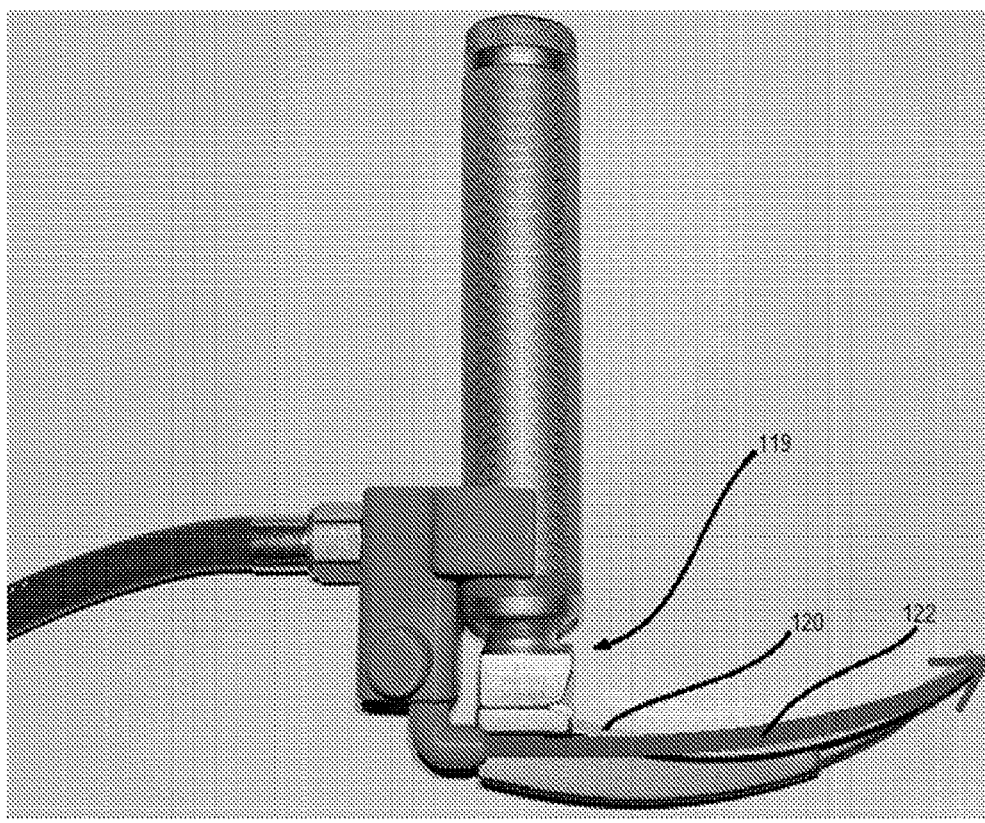
FIG. 12 is a photograph of an example of a device according to the present disclosure operatively coupled to a laryngoscope whilst having gas flow tubing secured to the gas flow inlet port, and while directing gas longitudinally along the lateral aspect of the laryngoscope blade.

In various examples, the gas flow nozzle 112 may also be configured to direct gas flows longitudinally along the lateral aspects 122 of the blade 120 of the laryngoscope 119, as indicated by the arrow in FIG. 12. In various examples, removeable nozzles may be secured through wedging, locking, rotation over threading, or the like. This gas flow nozzle 112 can be removable and interchangeable with other nozzles. The gas flow nozzle 112 can direct oxygen gas flows into the upper airways of patients such that the lower airways ultimately become oxygenated because of elevated upper airway oxygen tension, and diffusion of gas molecules, which ultimately results in the oxygenation of the patient. The gas flow nozzle 112 can direct flows of oxygen sufficient to cause an increase in airway pressure, which stents alveolar sacks open, preventing atelectasis, and thereby improving oxygenation and overall lung function.

Figure 10:
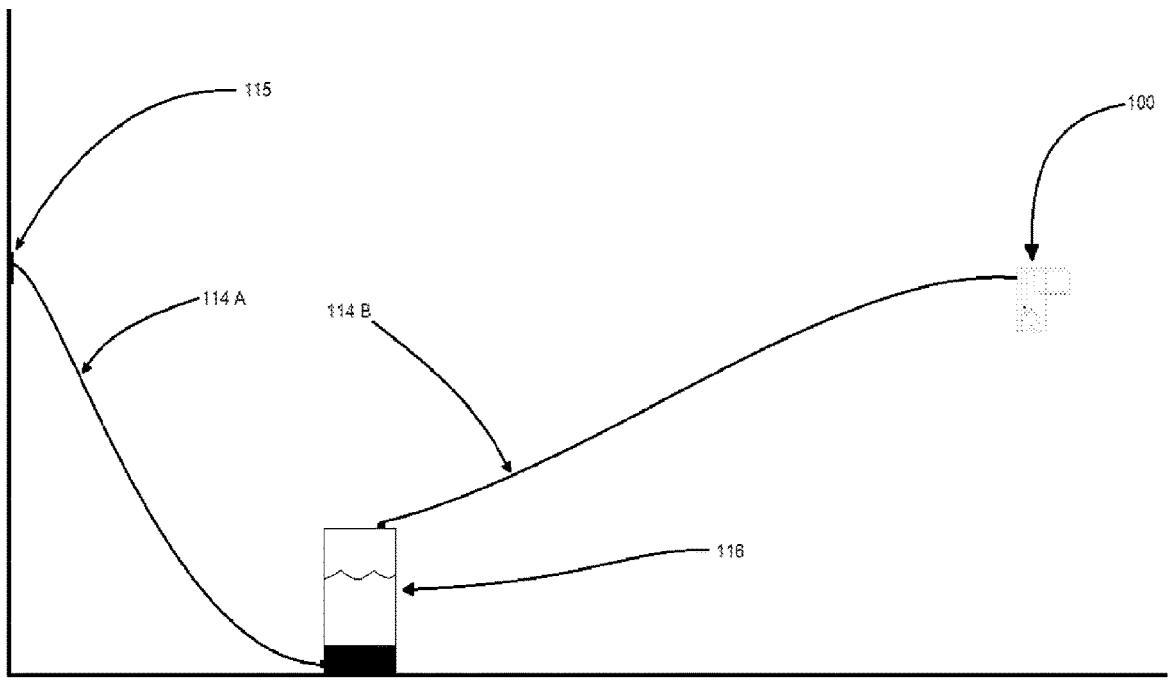
FIG. 10 is a side orthographic view of the device of FIG. 1, connected to a gas source via pre-humidification gas flow tubing that allows for the humidification of gas through a humidification apparatus, after which the humidified gas is carried to the device via post-humidification gas flow tubing.

Referring to FIG. 10, the gas flow regulator 103 may be separate from the housing 101 and thus the attachment apparatus 117 and gas flow nozzle 112. The gas flow regulator 103 can be located on a gas flow conduit anywhere between the gas source 115 and the gas flow nozzle 112. Furthermore, the gas flow regulator 103 may be attached to or integrated within the gas flow source entirely. This can result in the attachment apparatus 117, gas flow nozzle 112, and housing 101 that can be a unified unit, separate from the gas flow regulator 103. For example, the gas flow regulator 103 could be located at the gas source 115, and from there regulate gas flow through the gas flow tubing 114A and 114B, ultimately reaching the gas flow inlet port 102, traveling through the housing 101, exiting the gas flow outlet port 111 into the gas flow nozzle 112, which would then direct gas flows to the airway of the patient.

The gas flow inlet port 102 and gas flow outlet port 111 can be configured to accommodate various sizes (e.g., various diameters, wall thicknesses) of flow tubing 114A and 114B.

Gas from the gas flow source 115 can be optionally directed to a humidification chamber 116 via pre-humidification gas flow tubing 114A, and subsequently delivered to the device 100 via post-humidification gas flow tubing.

The components of the device according to the present disclosure may be fabricated from various materials such as, for example, rubbers, plastics, glass, ceramics, metals, silicones, and other materials.

Figure 6:
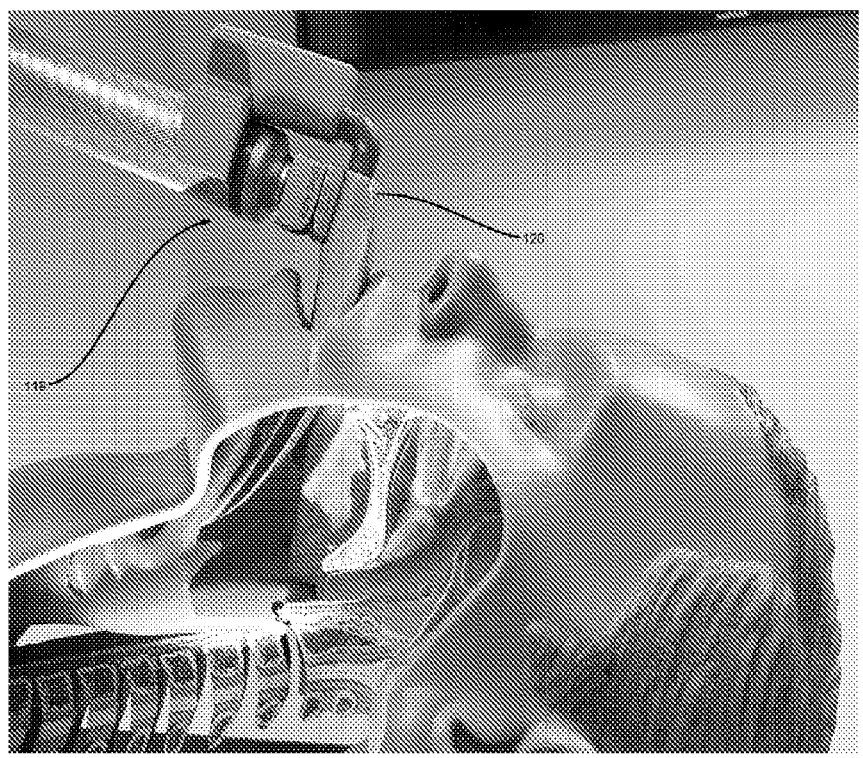
FIG. 6 is a photograph from a left-sided perspective of an example of a device according to the present disclosure operatively secured to a laryngoscope, actively performing laryngoscopy in the usual fashion.
Figure 7:
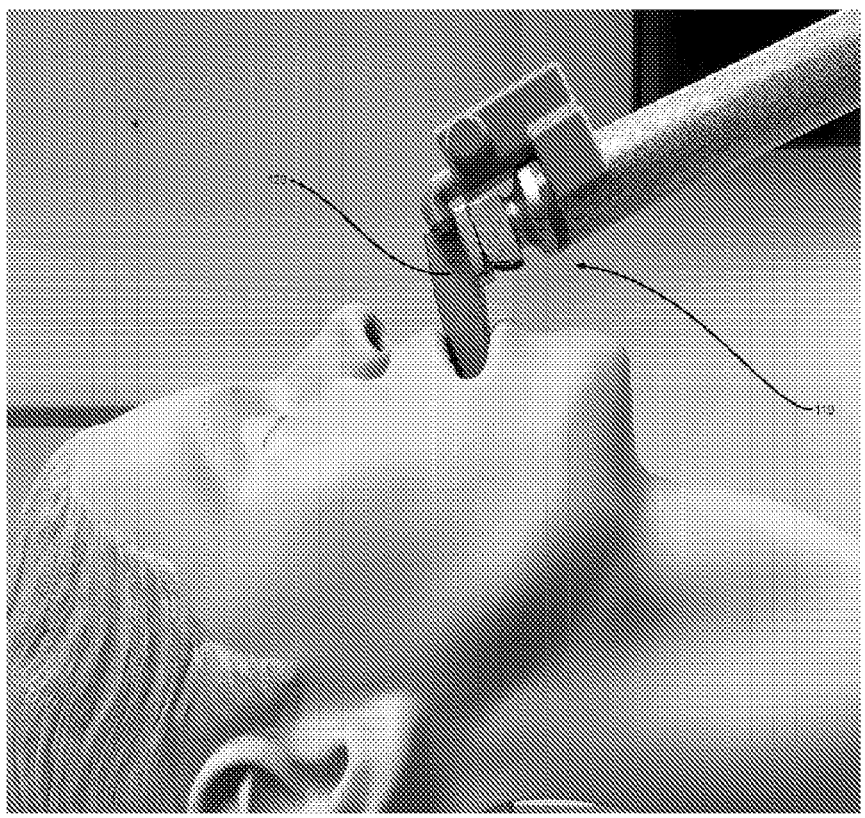
FIG. 7 is a photograph from a right-sided perspective of an example of a device according to the present disclosure operatively secured a laryngoscope, actively performing laryngoscopy in the usual fashion.
Figure 8:
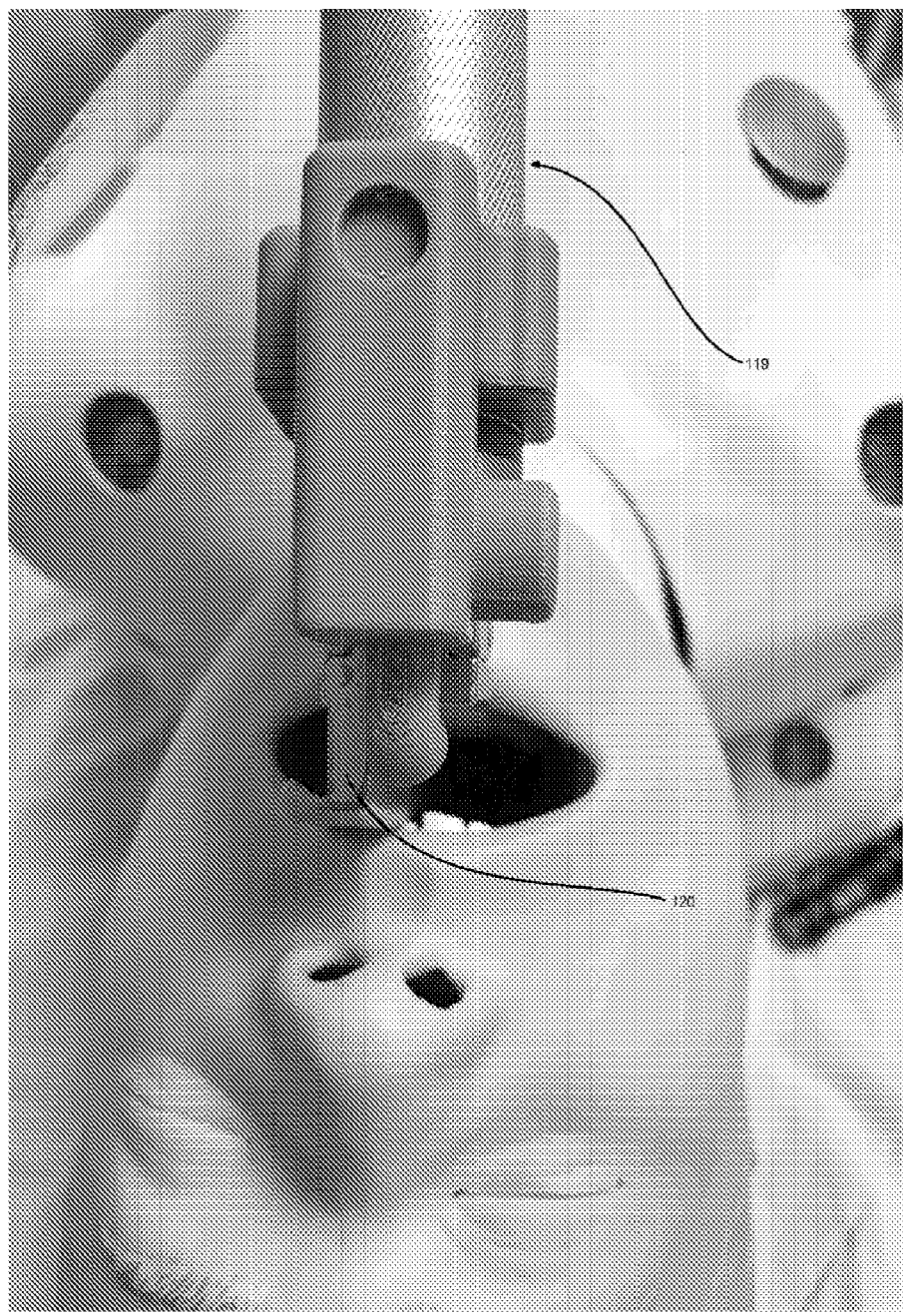
FIG. 8 is a photograph from an operator's perspective of an example of a device according to the present disclosure operatively secured to a laryngoscope, actively performing laryngoscopy in the usual fashion.
Figure 9:
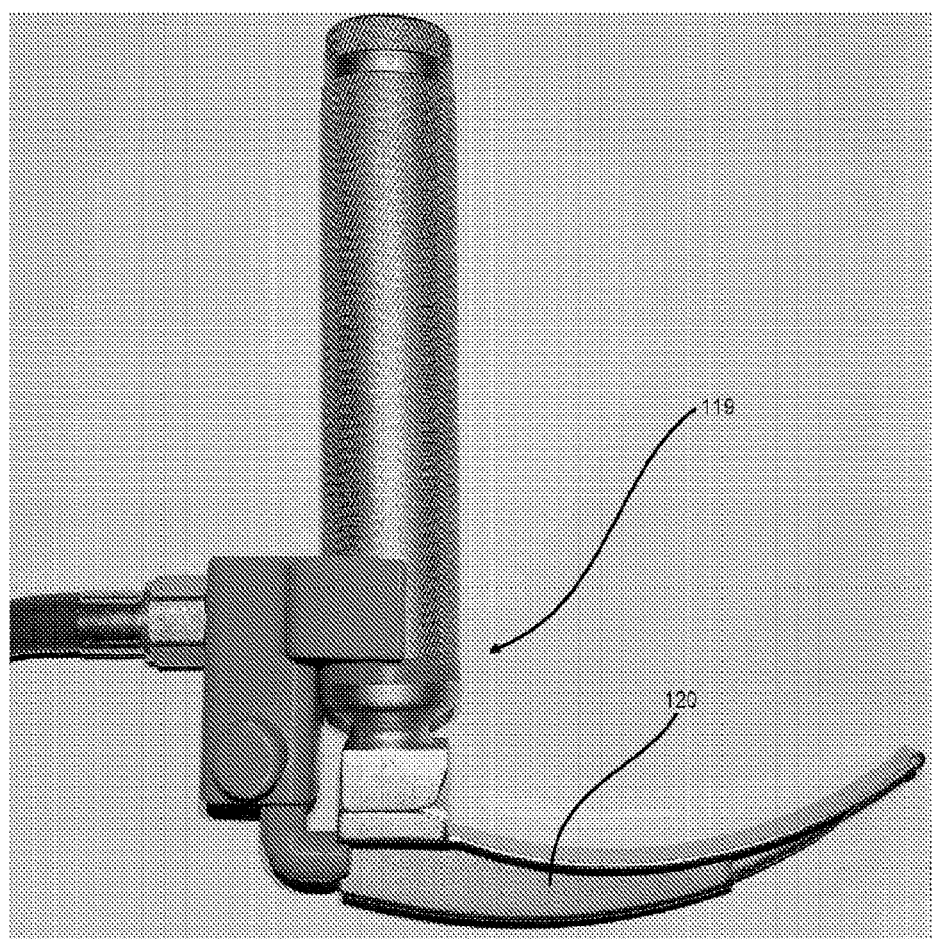
FIG. 9 is a photograph of an example of a device according to the present disclosure operatively coupled to a laryngoscope whilst having gas flow tubing secured to the gas flow inlet port.

Also provided are methods of using the device 100 during laryngoscopy. For example, after an anesthesiologist induces general anesthesia via inhaled or intravenous means, the anesthesiologist secures the airway device 100 connected to an oxygen source 115 to a laryngoscope. This may occur with or without using pre-humidification gas flow tubing 114A to carry the gas to a humidification apparatus 116 to humidify oxygen, which is then carried to the device 100 via post-humidification gas flow tubing 114B. The laryngoscope is then inserted into the patient's oral cavity as depicted in FIG. 6, FIG. 7, and FIG. 8. The gas flow nozzle 112, and/or the laryngoscope with the device 100 secured to it is maneuvered to optimally direct gas flows to the desired anatomical target, usually the glottic opening, or the laryngopharynx. The operator can then modulate the gas flow rate using the gas flow regulator 103, located either on the housing 101 or externally somewhere along the gas flow conduit, to further optimize oxygen flows. The operator can identify the precise gas flow rate by observing the bobbin or float 107 within the gas flow rate indicator 106 relative to the gas flow rate indicator markers 113. The device 100 increases oxygen tensions in the upper airways, ultimately translating to increased oxygen tensions in the lower airways, and thus oxygenating the patient while the patient is in an apneic state, while laryngoscopy is performed.

Figure 13:
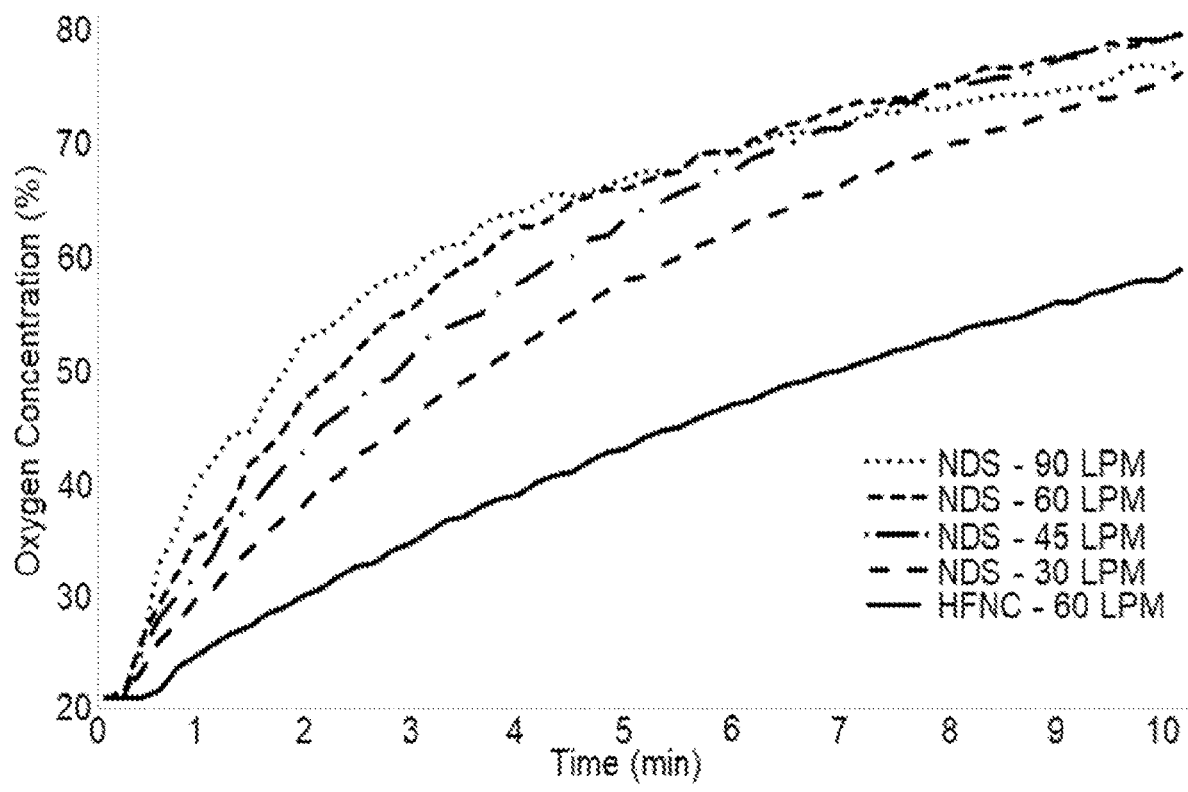
FIG. 13 is a chart displaying laboratory testing data.

Laboratory testing data is depicted in FIG. 13. A comparative high flow nasal cannula (HFNC) operating at 60 LPM was compared to a proof-of-concept device simulating the device 100 (NDS) set to operate at 30, 45, 60, and 90 LPM with a Cormack-Lehane (CL) grade I view. Testing was performed on an airway simulation mannequin. Distal airway oxygen concentration rise over time was the primary outcome of the test (higher is better). Airway oxygen concentrations at the beginning of the tests were 21%. The devices were applied at the specified flow rates and with a CL grade I view, and oxygen concentrations were recorded at 10-second intervals for a total of 10-minutes. The proof-of-concept device simulating the device 100 outperformed high flow nasal cannula at all flow rates.

Figure 14:
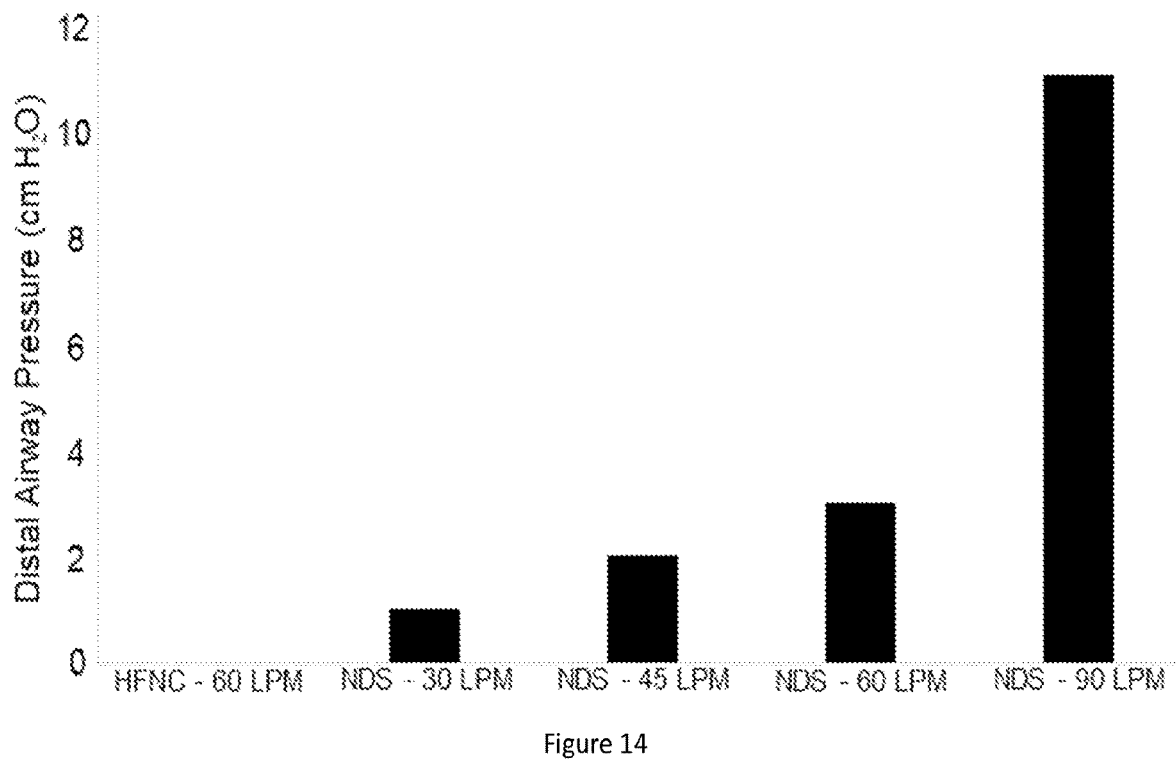
FIG. 14 is a chart displaying laboratory testing data.
Figure 15:
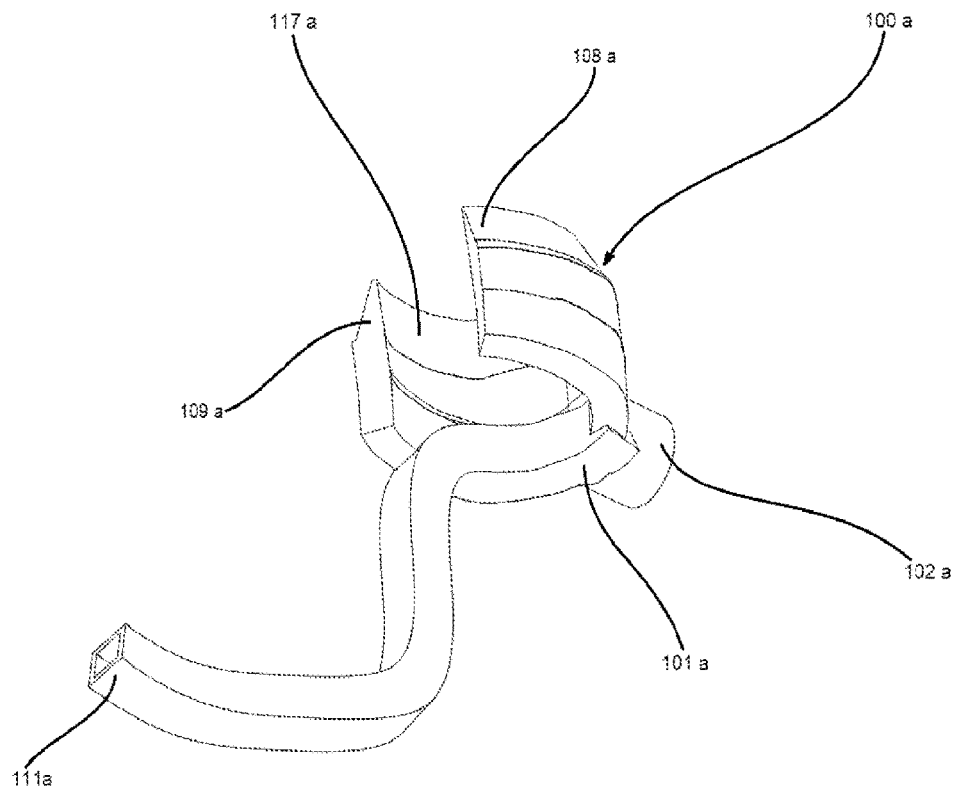
FIG. 15 is a left anteroinferior isometric view of an example of a device according to the present disclosure.
Figure 16:
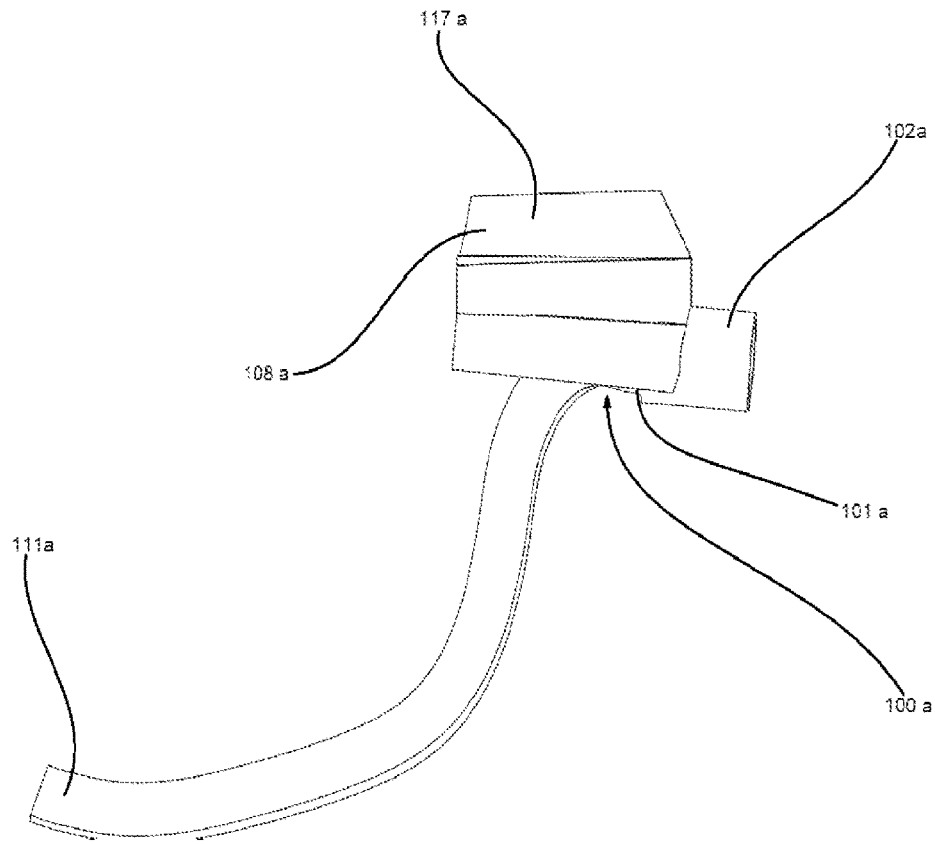
FIG. 16 is a left side orthographic view of the device of FIG. 15.
Figure 17:
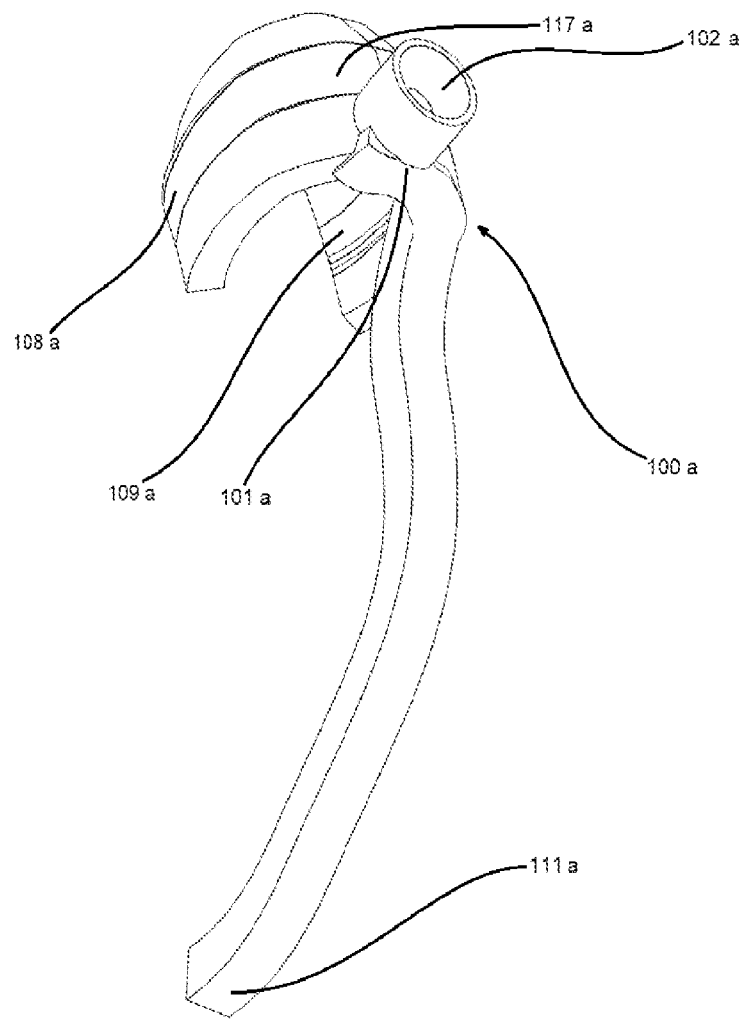
FIG. 17 is a left posteroinferior isometric view of the device of FIG. 15.
Figure 18:
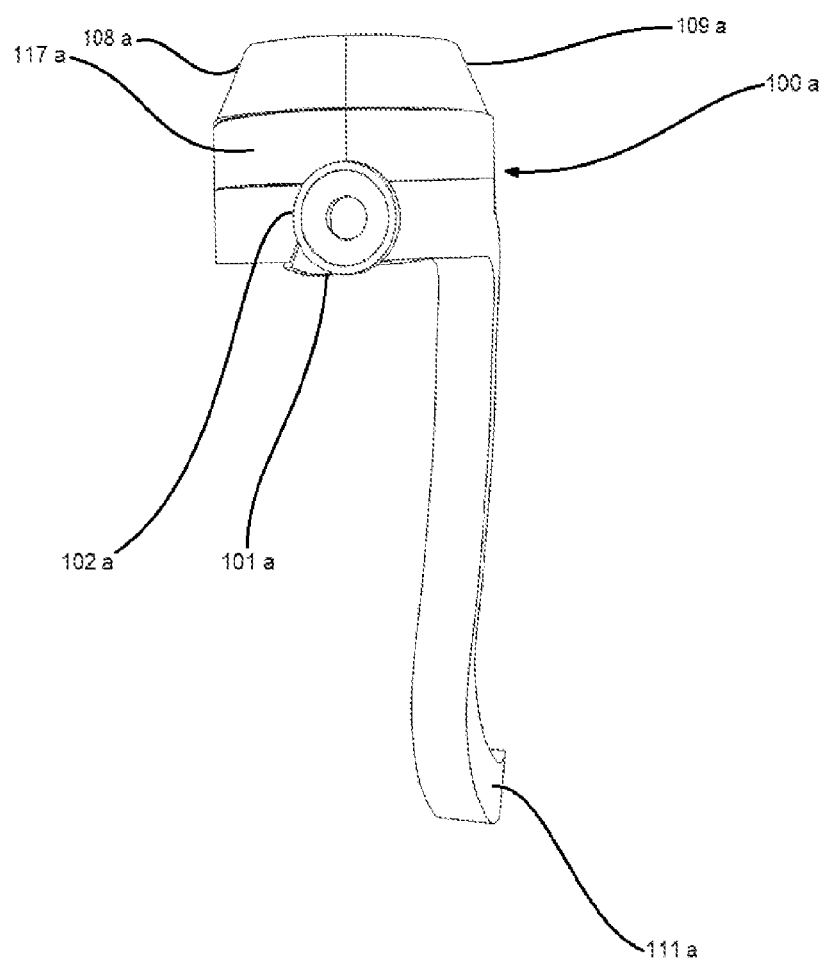
FIG. 18 is a rear orthographic view of the device of FIG. 15.
Figure 19:
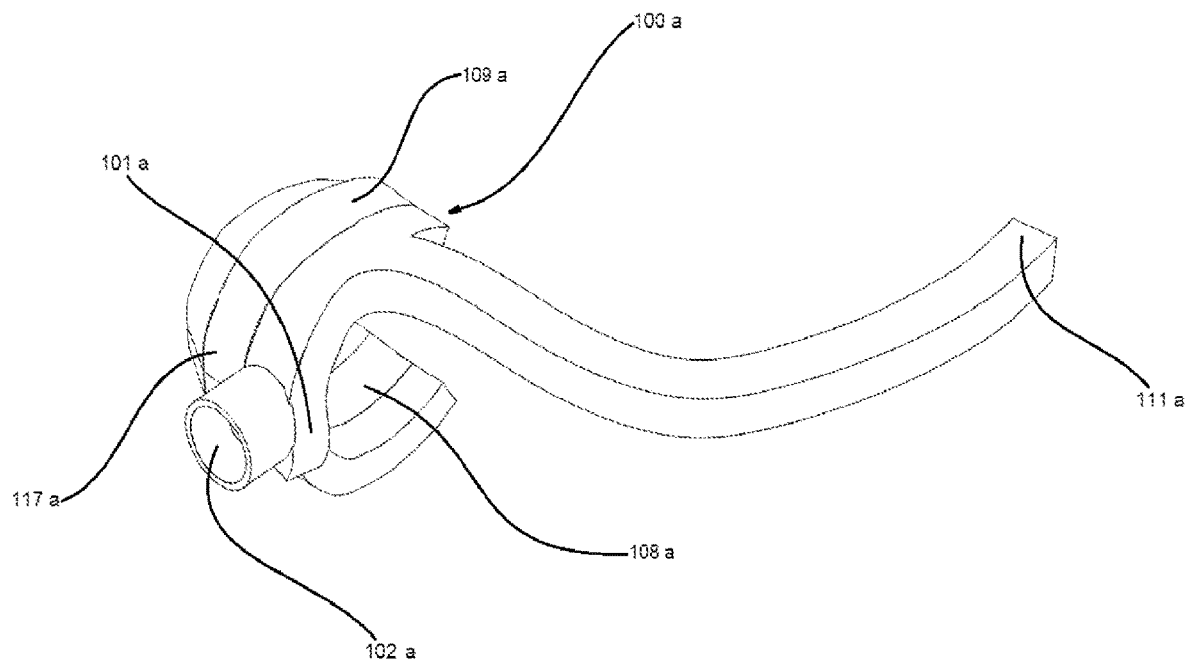
FIG. 19 is a right posteroinferior isometric view of the device of FIG. 15.
Figure 20:
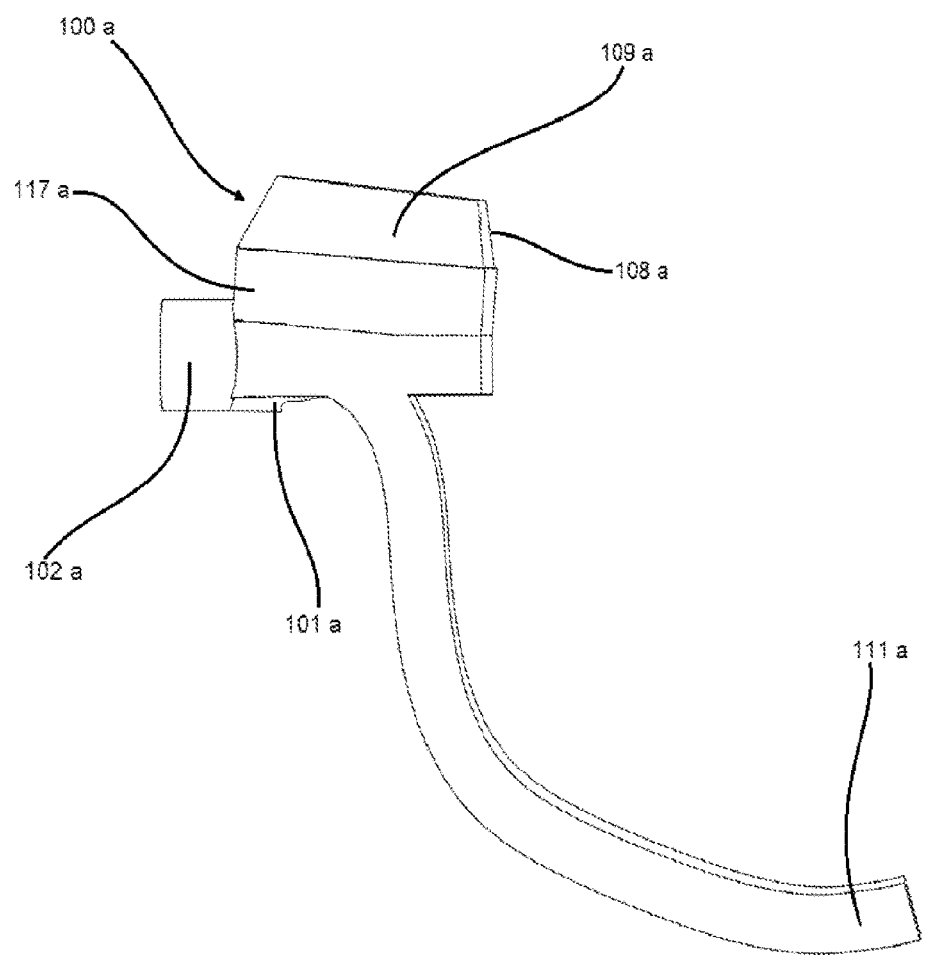
FIG. 20 is a right side orthographic view of the device of FIG. 15.

Laboratory testing data is depicted in FIG. 14. A comparative high flow nasal cannula (HFNC) operating at 60 LPM was compared to a proof-of-concept device simulating the device 100 (NDS) set to operate at 30, 45, 60, and 90 LPM with a Cormack-Lehane (CL) Grade I view. Testing was performed on an airway simulation mannequin. Mean distal airway pressure was the primary outcome of the test (higher is better). The devices were applied at the specified flow rates and with a CL grade I view, and airway pressures were recorded at 5-second intervals for a total of 2-minutes, and then averaged. The proof-of-concept device simulating the device 100 outperformed high flow nasal cannula at all flow rates.

Figure 28:
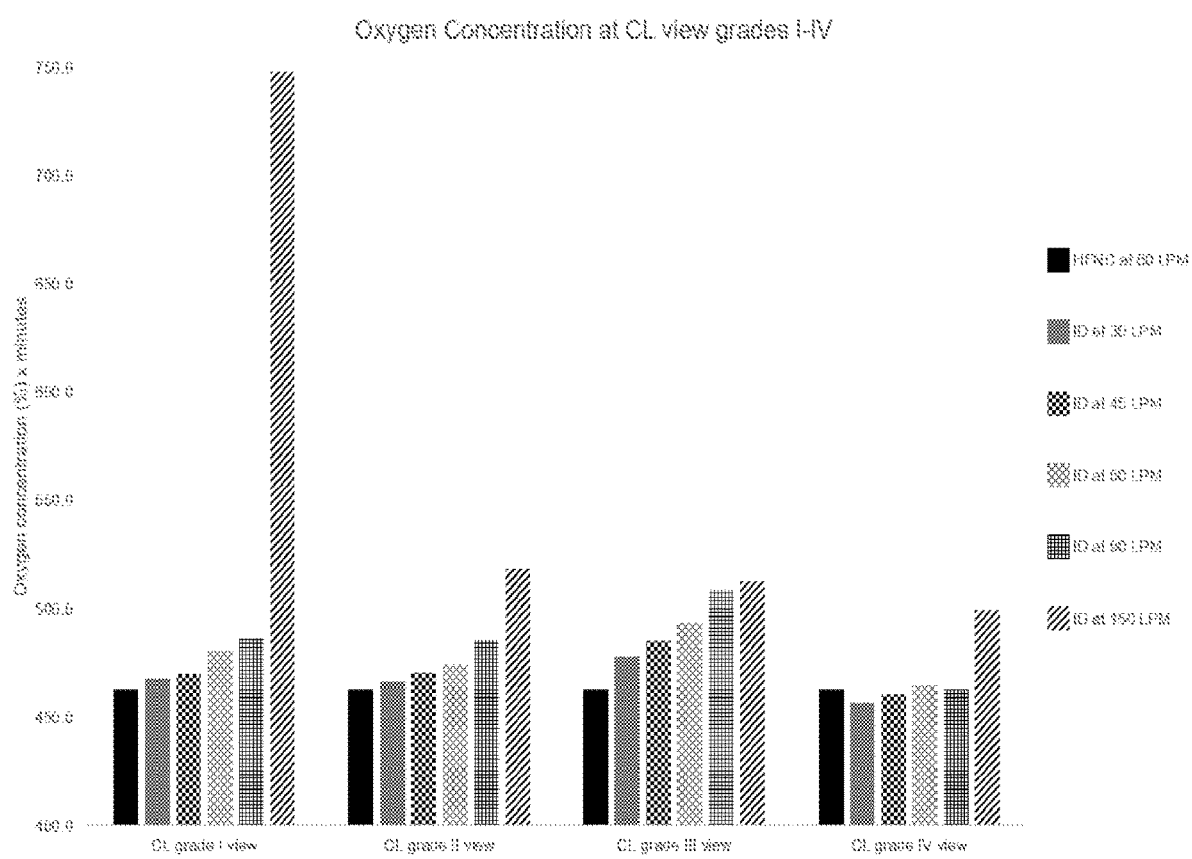
FIG. 28 is a chart displaying laboratory testing data.

Laboratory testing data is depicted in FIG. 28. A comparative high flow nasal cannula (HFNC) operating at 60 LPM was compared to the device 100a (ID) set to operate at 30, 45, 60, 90, and 150 LPM with Cormack-Lehane (CL) view grades I-IV. Testing was performed on an airway simulation mannequin. Distal airway oxygen concentration rise over time was the primary outcome of the test. Airway oxygen concentrations at the beginning of the tests were 21%. The devices were applied at the specified flow rates and CL view grades, and oxygen concentrations were recorded at 10-second intervals for a total of 10-minutes. Values of the bar graph reflect the total area under the curve at each flow rate with each CL view grade, expressed as oxygen concentration (%) x minutes (higher is better). The device 100a was non-inferior to or outperformed high flow nasal cannula at the various flow rates and view grades.

Figure 29:
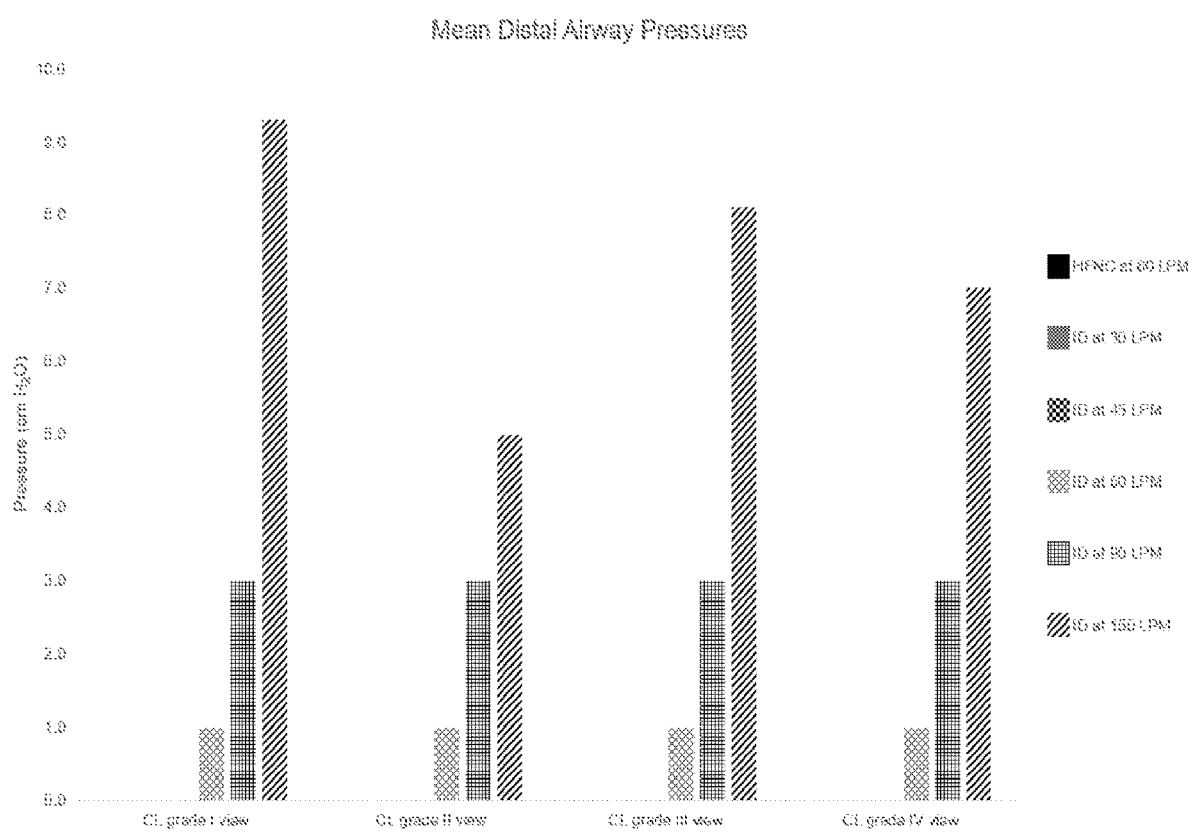
FIG. 29 is a chart displaying laboratory testing data.

Laboratory testing data is depicted in FIG. 29. A comparative high flow nasal cannula (HFNC) operating at 60 LPM was compared to the device 100a (ID) set to operate at 30, 45, 60, 90, and 150 LPM with Cormack-Lehane (CL) view grades I-IV. Testing was performed on an airway simulation mannequin. Mean distal airway pressure was the primary outcome of the test (higher is better). The devices were applied at the specified flow rates and CL view grades, and airway pressures were recorded at 5-second intervals for a total of 2-minutes, and then averaged. High flow nasal cannula produced no appreciable increase in mean airway pressures. The device 100a was non-inferior to or outperformed high flow nasal cannula at the various flow rates and view grades.

Figure 30:
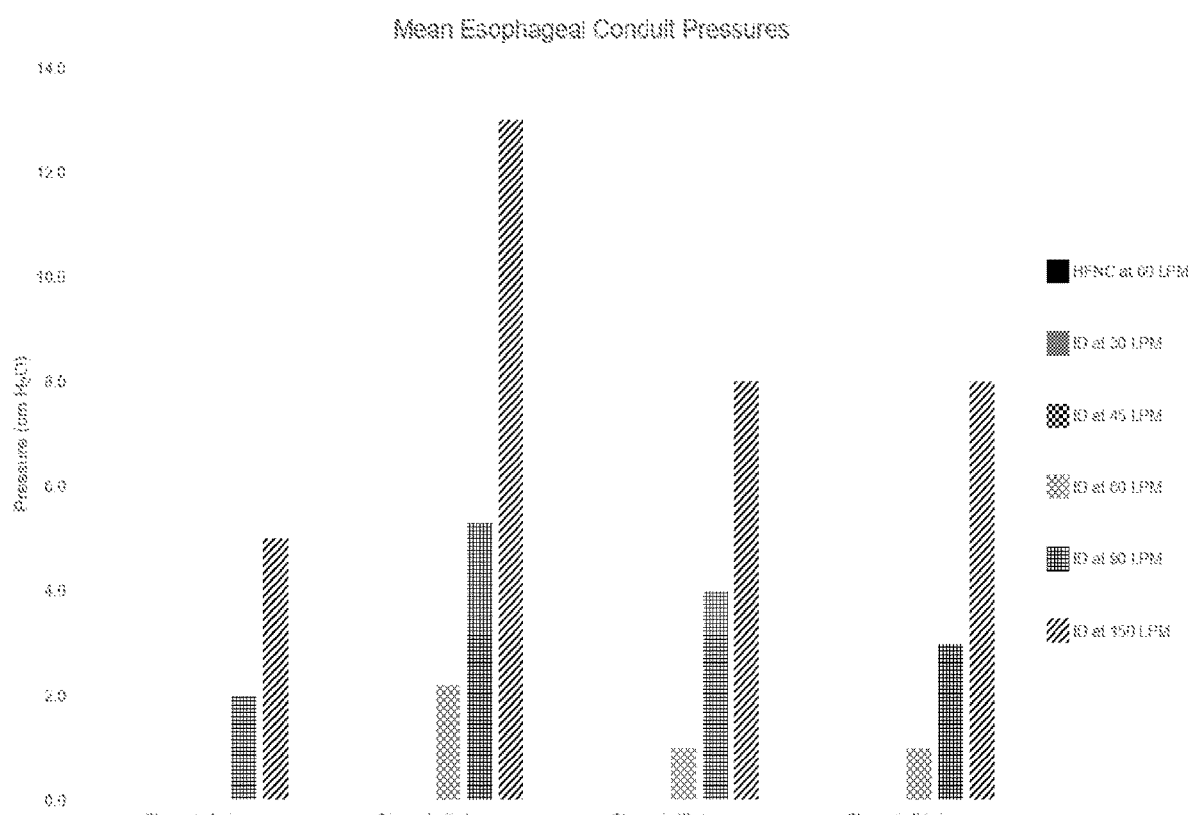
FIG. 30 is a chart displaying laboratory testing data.

Laboratory testing data is depicted in FIG. 30. A comparative high flow nasal cannula (HFNC) operating at 60 LPM was compared to the device 100a (ID) set to operate at 30, 45, 60, 90, and 150 LPM with Cormack-Lehane (CL) view grades I-IV. Testing was performed on an airway simulation mannequin. Average esophageal conduit pressure was the primary outcome of the test (less than 20 cm $H_2O$ is desirable). The devices were applied at the specified flow rates and CL view grades, and esophageal conduit pressures were recorded at 5-second intervals for a total of 2-minutes, and then averaged. The device 100a achieved esophageal conduit pressures less than 20 cm $H_2O$ at all flow rates and view grades.

The device 100 can allow for effective apneic oxygenation while being compact, and/or easily attached to a laryngoscope. This can enable airway managers, such as, for example, an anesthesiologist, nurse anesthetist, intensivist, emergency physician, surgeon, nurse practitioner, physician assistant, or paramedic to be adequately disencumbered while manipulating the airway of a patient while simultaneously administering effective apneic oxygenation. Because the device 100 can administer gas flows through the oral cavity, it can administer relatively high flows of gas to the airway, as compared other devices which administer gas flows through the nasal passages, which are fragile, narrow, and often not patent. Because the device is operatively coupled to a laryngoscope whilst having a directable gas flow nozzle 112, oxygen jets can easily be directed to anatomic regions, as compared to other nasal devices that cannot be directed. It is the combination of higher oxygen flows, and the ability to precisely direct the flows to specific anatomical targets that allows the device 100 to more effectively perform apneic oxygenation. Furthermore, gas flow rates may be so high through the device 100 that a tissue stenting effect may be exerted on airway tissue, thereby improving operator visualization of relevant anatomical structures. It is yet another advantage of the present invention that its user and patient interface elements thereon can be made from disposable or sterilizable materials, such as, for example, polymers (e.g., rubbers, plastics, silicones), glass, ceramics, metals, and other materials, thereby allowing for single use or multiple uses. The device 100 can be rapidly deployed and used with little to no training required for end users. The device 100 can eliminate barriers to achieving effective apneic oxygenation during airway manipulation, thereby improving the safety profile of potentially any airway manipulation, including but not limited to laryngoscopy, endotracheal intubation, bronchoscopy, cricothyrotomy, tracheostomy, jet ventilation, and airway examination.

The various aspects of what is described above can be used alone or in various combinations. It should be noted that the teachings of this application are not limited to the use in airway oxygenation but can be equally well applied to illuminating the airway, insufflating other gases or air, accessing the upper or lower airways, visualizing the airway with camera attachments or the like.

Although the teaching of the present application has been described in detail for the purpose of illustration, it is understood that such detail is solely for that purpose, and variations can be made therein by those skilled in the art without departing from the scope of the teaching of this application. For example, the device has been described with a housing 101 that is substantially angular and rectangular, but it is understood that this housing does not need to be angular or rectangular—the outline of the housing could have any other suitable shape that is used in these kinds of devices. Likewise, the device 100 has been illustrated to have a gas flow inlet port 102 on the upper rear face of the housing 101, and the gas flow outlet port 111 on the bottom face of the housing 101, but it is understood that the locations of the ports 102 and 111 need not be in these locations—they could be located in any location suitable for the task for which the device 100 is used. Further, the device 100 has been illustrated as one piece when fully assembled (gas flow nozzle 112 attached), but it is understood that the teaching can also be applied to devices that have several housing parts, separate from each other, but connected by gas flow conduits.

As another example, it should be noted that although the teaching of the present application has been described in the terms of airway management and human or animal oxygenation, it should be appreciated that the teachings of the present application may also be applied to other types of devices, such as a garden hose, paint sprayer, cooking utensil and the like for the purpose of applying an additional component, liquid, gas, or other. For example, the device 100 could be operatively coupled to a garden hose for the purpose of delivering fertilizer in conjunction with flows of water from the garden hose. As another example, the device 100 could be operatively coupled to a paint sprayer to administer additional chemicals to a coat of paint, in conjunction with paint being administered by the primary paint sprayer. The device 100 could also, for example, be operatively coupled to a butane lighter to administer ingredients in conjunction with the flame whilst cooking. It should also be noted that there are many alternative ways of implementing the methods and apparatuses of the teachings of the present application.

The following numbered clauses are directed to various non-limiting embodiments and aspects according to the present disclosure.

Clause 1. A device for operatively coupling to a laryngoscope for administration of a positive pressure to the airway of a mammal, the device comprising: a housing comprising a gas flow inlet port configured to receive a tube; an attachment apparatus operatively coupled to the housing and configured to operatively couple to the laryngoscope, the attachment apparatus comprising a first clamp arm and a second clamp arm; a gas flow nozzle operatively coupled to the housing and configured to direct a flow of gas down a longitudinal axis of a buccal aspect of a blade of laryngoscope, the gas flow nozzle comprising a gas flow outlet port, a gas flow conduit defined in the housing and the gas flow nozzle to form fluid communication between the gas flow inlet port and the gas flow outlet port.

Clause 2. The device of clause 1, wherein the attachment apparatus is configured to friction fit to the laryngoscope.

Clause 3. The device of any one of clauses 1-2, wherein the first clamp arm and the second clamp arm are curved inward towards one another.

Clause 4. The device of any one of clauses 1-3, wherein the first clamp arm, the second clamp arm, and the gas flow nozzle extend away from the housing in substantially the same direction.

Clause 5. The device of any one of clauses 1-4, wherein the gas flow nozzle extends away from the housing a first distance in a first direction and the attachment apparatus extends away from the housing a second distance in the first direction, wherein the first distance is greater than the second distance.

Clause 6. The device of any one of clauses 1-5, wherein the attachment apparatus further comprises, a clamp hinge, wherein the first clamp arm pivotally coupled to the clamp hinge and the second clamp arm pivotally coupled to the clamp hinge; and a spring configured to urge the first clamp arm towards the second clamp arm.

Clause 7. The device any one of clauses 1-6, wherein the attachment apparatus further comprises a magnet.

Clause 8. The device of any one of clauses 1-7, wherein the housing, the attachment apparatus, and the gas flow nozzle are integral.

Clause 9. The device of any one of clauses 1-7, wherein the gas flow nozzle is separate from the housing.

Clause 10. The device of any one of clauses 1-9, wherein the gas flow inlet port, gas flow outlet port, and gas flow conduit are sized and configured to enable a gas flow in a range of greater than 0 liters per minute to 250 liters per minute as measured with a 54 pounds per square inch gauge pressure feed at the gas inlet port and the gas flow outlet port open to atmospheric pressure.

Clause 11. The device of any one of clauses 1-10, wherein the gas flow inlet port, gas flow outlet port, and gas flow conduit are sized and configured to enable a gas flow in a range of greater than 25 liters per minute to 250 liters per minute as measured with a 54 pounds per square inch gauge pressure feed at the gas inlet port and the gas flow outlet port open to atmospheric pressure.

Clause 12. The device of any one of clauses 1-11, further comprising a gas flow regulator configured to control a rate of gas flow through the gas flow conduit.

Clause 13. The device of any one of clauses 1-12, wherein the gas flow nozzle is configured to direct gas at a desired location by movement of the gas flow nozzle relative to the housing, wherein the movement includes rotation, axial extension, flexion, torsion, or elongation of the shape of the gas flow nozzle.

Clause 14. The device of any one of clauses 1-13, wherein the gas flow regulator is separate from the housing.

Clause 15. The device of any one of clauses 1-13, wherein the gas flow regulator is integral with the housing.

Clause 16. The device of clause 15, wherein the gas flow regulator further comprises a gas flow controller.

Clause 17. The device of any one of clauses 1-16, wherein the laryngoscope is a simple laryngoscope or a video laryngoscope.

Clause 18. The device of any one of clauses 1-17, wherein the device is used to insufflate the airway with any necessary gas.

Clause 19. A device for operatively coupling to a laryngoscope for administration of a positive pressure to the airway of a mammal, the device comprising: a housing comprising a gas flow inlet port configured to receive a tube; an attachment apparatus operatively coupled to the housing and configured to operatively couple to the laryngoscope, the attachment apparatus comprising a first clamp arm and a second clamp arm that are configured to friction fit to the laryngoscope, and the first clamp arm and the second clamp arm are curved inward towards the other; and a gas flow nozzle operatively coupled to the housing and configured to direct a flow of gas down a longitudinal axis of a buccal aspect of a blade of laryngoscope, the gas flow nozzle comprising a gas flow outlet port, a gas flow conduit defined in the housing and the gas flow nozzle to form fluid communication between the gas flow inlet port and the gas flow outlet port, wherein the gas flow inlet port, gas flow outlet port, and gas flow conduit are sized and configured to enable a gas flow in a range of greater than 0 liters per minute to 250 liters per minute as measured with a 54 pounds per square inch gauge pressure feed at the gas inlet port and the gas flow outlet port open to atmospheric pressure, and wherein the housing, the attachment apparatus, and the gas flow nozzle are integral.

Clause 20. A method of laryngoscopy comprising: operatively coupling a gas source to a simple laryngoscope or video laryngoscope for administration of a positive pressure to the airway of a mammal utilizing the device of any one of clauses 1-19; and insufflating the airway of the mammal with the device.

Clause 21. A device for operatively coupling to a structure and directing gas flow, the device comprising: an attachment apparatus configured to operatively couple to the structure; a gas flow nozzle configured to direct a flow of gas; and a housing operatively coupled to the attachment apparatus and to the gas outlet nozzle.

Clause 22. The device of clause 1, wherein the housing comprises a gas flow inlet port, a gas flow outlet port, and a gas flow conduit connecting the gas flow inlet to the gas flow outlet, wherein the gas flow nozzle is configured to be operatively coupled to the gas flow outlet port or is integral with the gas flow outlet port.

Clause 23. The device according to clause 2, further comprising a gas flow regulator configured to control a rate of gas flow through the gas flow conduit.

Clause 24. The device according to any of clauses 1-3, wherein the attachment apparatus comprises: a clamp hinge; a first clamp arm pivotally coupled to the clamp hinge; a second clamp arm pivotally coupled to the clamp hinge; a spring configured to urge the first clamp arm towards the second clamp arm.

Clause 25. The device according to any of clauses 20-24, wherein the attachment apparatus comprises a magnet.

Clause 26. The device according to any of clauses 20-25, wherein the attachment apparatus comprises a shape suitable to attach to a laryngoscope.

Clause 27. The device according to any of clauses 20-26, wherein the gas flow nozzle is secured temporarily to the gas flow outlet port.

Clause 28. The device according to any of clause 20-26, wherein the gas flow nozzle is integral with the gas flow outlet port.

Clause 29. The device according to any of clause 20-28, wherein the gas flow nozzle is disposable.

Clause 30. The device according to any of clauses 20-29, wherein the gas flow nozzle is reusable.

Clause 31. The device according to any of clauses 20-30, wherein the gas flow nozzle is configured to direct gas at a desired location by movement of the gas flow nozzle relative to the housing.

Clause 32. The device according to clause 31, wherein the movement includes rotation, axial extension, flexion, torsion, or elongation of the shape of the gas flow nozzle.

Clause 33. The device according to any of clauses 21-32, wherein the gas flow nozzle may be directed down the longitudinal axis of the buccal aspect of the laryngoscope blade.

Clause 34. The device according to any of clauses 22-33, wherein the gas flow inlet port, gas flow outlet port, and gas flow conduit are sized and configured to enable a gas flow in a range of greater than 0 liters per minute to 250 liters per minute.

Clause 35. The device according to any of clauses 20-34, wherein the device is configured to direct gas flow to an airway of a mammal.

Clause 36. The device according to any of clauses 22-35, wherein the gas flow regulator is separate from the attachment apparatus.

Clause 37. The device according to any of clauses 22-35, wherein the gas flow regulator is integral with the housing.

Clause 38. The device according to any of clauses 22-35, wherein the gas flow regulator may be located between the gas source and the gas flow inlet port, separate from the housing.

Clause 39. The device according to any of clauses 22-35, wherein the gas flow regulator further comprises a gas flow controller.

Clause 40. The device according to any of clauses 22-39, wherein the structure is a laryngoscope, a video laryngoscope, a bronchoscope, or an endotracheal tube.

Clause 41. The device according to any of claims 20-40, wherein the device is used to perform oxygenation when used in conjunction with oxygen.

Clause 42. The device according to claim any of clauses 20-41, wherein the device is used to insufflate the airway with any necessary gas.

Clause 43. A method of laryngoscopy comprising: operatively coupling a gas source to a laryngoscope or video laryngoscope for administration of a positive pressure to the airway of a mammal utilizing the device of any of the preceding clauses.

Additionally, it should be noted that features described in the preceding descriptions may be used in combinations other than the combination explicitly described.

Whilst endeavoring in the foregoing specification to draw attention to those features of the invention believed to be of particular importance it should be understood that the applicant claims protection in respect of any patentable feature or combination of features hereinbefore referred to and/or shown in the drawings whether or not particular emphasis has been placed thereon.

Any references herein to "various examples," "some examples," "one example," "an example," or like phrases mean that a particular feature, structure, or characteristic described in connection with the example is included in at least one example. Thus, appearances of the phrases "in various examples," "in some examples," "in one example," "in an example," or like phrases in the specification do not necessarily refer to the same example. Furthermore, the particular described features, structures, or characteristics may be combined in any suitable manner in one or more examples. Thus, the particular features, structures, or characteristics illustrated or described in connection with one example may be combined, in whole or in part, with the features, structures, or characteristics of one or more other examples without limitation. Such modifications and variations are intended to be included within the scope of the present examples.

In this specification, unless otherwise indicated, all numerical parameters are to be understood as being prefaced and modified in all instances by the term "about," in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described herein should at least be construed in light of the number of reported significant digits and by applying ordinary rounding techniques.

Any numerical range recited herein includes all sub-ranges subsumed within the recited range. For example, a range of "1 to 10" includes all sub-ranges between (and including) the recited minimum value of 1 and the recited maximum value of 10, that is, having a minimum value equal to or greater than 1 and a maximum value equal to or less than 10. Also, all ranges recited herein are inclusive of the end points of the recited ranges. For example, a range of "1 to 10" includes the end points 1 and 10. Any maximum numerical limitation recited in this specification is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited. All such ranges are inherently described in this specification.

The grammatical articles "a," "an," and "the," as used herein, are intended to include "at least one" or "one or more," unless otherwise indicated, even if "at least one" or "one or more" is expressly used in certain instances. Thus, the foregoing grammatical articles are used herein to refer to one or more than one (i.e., to "at least one") of the particular identified elements. Further, the use of a singular noun includes the plural, and the use of a plural noun includes the singular, unless the context of the usage requires otherwise.

The term "comprising" as used in the claims does not exclude other elements or steps. The term "a" or "an" as used in the claims does not exclude a plurality. A unit or other means may fulfill the functions of several units or means recited in the claims.

One skilled in the art will recognize that the herein described batteries, structures, operations/actions, and objects, and the discussion accompanying them, are used as examples for the sake of conceptual clarity and that various configuration modifications are contemplated. Consequently, as used herein, the specific examples set forth and the accompanying discussion are intended to be representative of their more general classes. In general, use of any specific exemplar is intended to be representative of its class, and the non-inclusion of specific components, devices, apparatus, operations/actions, and objects should not be taken as limiting. While the present disclosure provides descriptions of various specific aspects for the purpose of illustrating various aspects of the present disclosure and/or its potential applications, it is understood that variations and modifications will occur to those skilled in the art. Accordingly, the invention or inventions described herein should be understood to be at least as broad as they are claimed and not as more narrowly defined by particular illustrative aspects provided herein.

What is claimed is:

1. A device for operatively coupling to a laryngoscope for administration of a positive pressure to an airway of a mammal, the device comprising:
    a housing comprising a gas flow inlet port configured to receive a tube;
    an attachment apparatus operatively coupled to the housing and configured to operatively couple to the laryngoscope, the attachment apparatus comprising a first clamp arm and a second clamp arm; and
    a gas flow nozzle operatively coupled to the housing and configured to direct a flow of gas down a longitudinal axis of a buccal aspect of a blade of laryngoscope, the gas flow nozzle comprising a gas flow outlet port, a gas flow conduit defined in the housing and the gas flow nozzle to form fluid communication between the gas flow inlet port and the gas flow outlet port,
    wherein the gas flow inlet port, gas flow outlet port, and gas flow conduit are sized and configured to enable a gas flow in a range of greater than 0 liters per minute to 250 liters per minute as measured with a 54 pounds per square inch gauge pressure feed at the gas flow inlet port and the gas flow outlet port open to atmospheric pressure.

2. The device of claim 1, wherein the attachment apparatus is configured to friction fit to the laryngoscope.

3. The device of claim 1, wherein the first clamp arm and the second clamp arm are curved inward towards one another.

4. The device of claim 1, wherein the first clamp arm, the second clamp arm, and the gas flow nozzle extend away from the housing in substantially the same direction.

5. The device of claim 1, wherein the gas flow nozzle extends away from the housing a first distance in a first direction and the attachment apparatus extends away from the housing a second distance in the first direction, wherein the first distance is greater than the second distance.

6. The device of claim 1, wherein the attachment apparatus further comprises:
    a clamp hinge, wherein the first clamp arm pivotally coupled to the clamp hinge and the second clamp arm pivotally coupled to the clamp hinge; and
    a spring configured to urge the first clamp arm towards the second clamp arm.

7. The device of claim 1, wherein the attachment apparatus further comprises a magnet.

8. The device of claim 1, wherein the housing, the attachment apparatus, and the gas flow nozzle are integral.

9. The device of claim 1, wherein the gas flow nozzle is separate from the housing.

10. The device of claim 1, wherein the gas flow inlet port, gas flow outlet port, and gas flow conduit are sized and configured to enable a gas flow in a range of greater than 25 liters per minute to 250 liters per minute as measured with a 54 pounds per square inch gauge pressure feed at the gas flow inlet port and the gas flow outlet port open to atmospheric pressure.

11. The device of claim 1, further comprising a gas flow regulator configured to control a rate of gas flow through the gas flow conduit.

12. The device of claim 1, wherein the gas flow nozzle is configured to direct gas at a desired location by movement of the gas flow nozzle relative to the housing, wherein the movement includes rotation, axial extension, flexion, torsion, or elongation of a shape of the gas flow nozzle.

13. The device of claim 11, wherein the gas flow regulator is separate from the housing.

14. The device of claim 11, wherein the gas flow regulator is integral with the housing.

15. The device of claim 14, wherein the gas flow regulator further comprises a gas flow controller.

16. A system comprising:
   the device of claim 1; and
   a simple laryngoscope or a video laryngoscope operatively coupled to the device.

17. The device of claim 1, wherein the device is adapted for use to insufflate the airway with any necessary gas.

18. A device for operatively coupling to a laryngoscope for administration of a positive pressure to an airway of a mammal, the device comprising:
   a housing comprising a gas flow inlet port configured to receive a tube;
   an attachment apparatus operatively coupled to the housing and configured to operatively couple to the laryngoscope, the attachment apparatus comprising a first clamp arm and a second clamp arm that are configured to friction fit to the laryngoscope; and
   a gas flow nozzle operatively coupled to the housing and configured to direct a flow of gas down a longitudinal axis of a buccal aspect of a blade of laryngoscope, the gas flow nozzle comprising a gas flow outlet port, a gas flow conduit defined in the housing and the gas flow nozzle to form fluid communication between the gas flow inlet port and the gas flow outlet port,
   wherein the gas flow inlet port, gas flow outlet port, and gas flow conduit are sized and configured to enable a gas flow in a range of greater than 0 liters per minute to 250 liters per minute as measured with a 54 pounds per square inch gauge pressure feed at the gas flow inlet port and the gas flow outlet port open to atmospheric pressure, and
   wherein the housing, the attachment apparatus, and the gas flow nozzle are integral.

19. A method of laryngoscopy comprising:
   operatively coupling a gas source to a simple laryngoscope or video laryngoscope for administration of a positive pressure to an airway of a mammal utilizing the device of claim 1; and
   insufflating the airway of the mammal with the device.

* * * * *